(12) United States Patent
Vase

(10) Patent No.: US 12,383,714 B2
(45) Date of Patent: Aug. 12, 2025

(54) SYSTEMS, CATHETERS, AND METHODS FOR TREATING ALONG THE CENTRAL NERVOUS SYSTEM

(71) Applicant: MINNETRONIX NEURO, INC., St. Paul, MN (US)

(72) Inventor: Abhi Vase, Los Altos Hills, CA (US)

(73) Assignee: MINNETRONIX NEURO, INC., St.Paul, MN (US)

( * ) Notice: Subject to any disclaimer, the term of this patent is extended or adjusted under 35 U.S.C. 154(b) by 1543 days.

(21) Appl. No.: 16/536,239

(22) Filed: Aug. 8, 2019

(65) Prior Publication Data
US 2020/0046952 A1 Feb. 13, 2020

Related U.S. Application Data

(60) Provisional application No. 62/844,566, filed on May 7, 2019, provisional application No. 62/716,335, filed on Aug. 8, 2018.

(51) Int. Cl.
*A61M 27/00* (2006.01)
*A61B 5/00* (2006.01)
(Continued)

(52) U.S. Cl.
CPC .......... *A61M 27/006* (2013.01); *A61B 5/021* (2013.01); *A61B 5/026* (2013.01); *A61B 5/031* (2013.01); *A61B 5/14542* (2013.01); *A61B 5/14546* (2013.01); *A61B 5/4064* (2013.01); *A61B 5/407* (2013.01); *A61B 5/7275* (2013.01); *A61M 25/003* (2013.01); *G16H 20/40* (2018.01); *G16H 50/20* (2018.01); *G16H 50/30* (2018.01);
(Continued)

(58) Field of Classification Search
CPC .... A61M 27/006; A61M 27/002; A61M 5/14; A61M 25/003; A61M 25/007; A61M 2025/0057; A61M 2202/0464; A61M 2202/203; A61M 2205/3334; A61M 2205/3344; A61M 2205/3379; A61M 2205/3606; A61M 2205/50; A61M 2205/502; A61M 2205/52; A61M 2205/75; A61M 2210/0496; A61B 5/021; A61B 5/026; A61B 5/031; A61B 5/14542; A61B 5/14546; A61B 5/4064; A61B 5/407
See application file for complete search history.

(56) References Cited

U.S. PATENT DOCUMENTS 8,435,204 B2  5/2013  Lad et al.
9,536,052 B2  1/2017  Amarasingham et al.
(Continued)

*Primary Examiner* — Philip R Wiest
(74) *Attorney, Agent, or Firm* — Seager, Tufte & Wickhem LLP

(57) ABSTRACT

Systems, catheters, and methods for accessing and treating along the central nervous system are disclosed. An example method may manage inflammation of the patient to treat a condition of the patient by processing values related to one or more physiological parameters of a patent, identifying when an inflammation condition of the patient has reached a treatment condition based on the processed values, and automatically providing an indication that the inflammation condition has reached the treatment condition. An example indication may include actuation of a treatment protocol. The example method may be performed with an inflammation management system.

20 Claims, 6 Drawing Sheets

(51) Int. Cl.
*A61B 5/021* (2006.01)
*A61B 5/026* (2006.01)
*A61B 5/03* (2006.01)
*A61B 5/145* (2006.01)
*A61M 25/00* (2006.01)
*G16H 20/40* (2018.01)
*G16H 50/20* (2018.01)
*G16H 50/30* (2018.01)
*A61B 5/024* (2006.01)
*A61M 5/14* (2006.01)

(52) U.S. Cl.
CPC ............... *A61B 5/024* (2013.01); *A61M 5/14* (2013.01); *A61M 2025/0057* (2013.01); *A61M 25/007* (2013.01); *A61M 2202/0464* (2013.01); *A61M 2202/07* (2013.01); *A61M 2202/203* (2013.01); *A61M 2205/3334* (2013.01); *A61M 2205/3344* (2013.01); *A61M 2205/3379* (2013.01); *A61M 2205/3606* (2013.01); *A61M 2205/50* (2013.01); *A61M 2205/502* (2013.01); *A61M 2205/52* (2013.01); *A61M 2205/75* (2013.01); *A61M 2210/0693* (2013.01); *A61M 2210/1003* (2013.01); *A61M 2230/04* (2013.01); *A61M 2230/06* (2013.01); *A61M 2230/20* (2013.01); *A61M 2230/50* (2013.01); *A61M 2230/63* (2013.01)

(56) References Cited

U.S. PATENT DOCUMENTS

| | | | |
|---|---|---|---|
| 9,864,840 B2 | 1/2018 | Grady et al. | |
| 10,569,064 B2 * | 2/2020 | Vase | A61F 7/00 |
| 2008/0058773 A1 * | 3/2008 | John | A61N 1/37235 |
| | | | 604/891.1 |
| 2012/0060622 A1 * | 3/2012 | Harris | A61B 5/031 |
| | | | 73/861 |
| 2015/0094644 A1 * | 4/2015 | Lenihan | A61M 39/24 |
| | | | 604/9 |
| 2016/0051801 A1 * | 2/2016 | Vase | A61M 25/0068 |
| | | | 604/8 |
| 2016/0287111 A1 * | 10/2016 | Jacobsen | A61B 5/002 |
| 2017/0095649 A1 * | 4/2017 | Vase | A61M 27/006 |

* cited by examiner

SYSTEMS, CATHETERS, AND METHODS FOR TREATING ALONG THE CENTRAL NERVOUS SYSTEM

CROSS-REFERENCE TO RELATED APPLICATIONS

This application claims the benefit of priority under 35 U.S.C. § 119 to U.S. Provisional Application Ser. No. 62/716,335, filed Aug. 8, 2018; and U.S. Provisional Application Ser. No. 62/844,566, filed May 7, 2019, the entirety of which are incorporated herein by reference.

TECHNICAL FIELD

The present disclosure relates to systems, modules, and methods for diagnosing and treating along the central nervous system.

BACKGROUND

A wide variety of medical devices, systems, and methods have been developed for medical use. Some of these devices, systems, and methods include control systems, pumps, guidewires, catheters, and the like. These devices and systems are manufactured by any one of a variety of different manufacturing methods and may be used according to any one of a variety of methods. Of the known medical devices, systems, and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices and/or systems. One example includes an inflammation management system. The system comprises: a controller; a cerebrospinal fluid management module in communication with the controller; wherein the controller is configured to: monitor measurements of one or more physiological parameters of a patient; compare a value related to the monitored measurements of the one or more physiological parameters to a threshold value; and control the cerebrospinal fluid management module based on the comparison of the value related to the monitored measurements of the one or more physiological parameters to the threshold value.

Alternatively or additionally to any of the embodiments above, wherein the controller is configured to automatically control the cerebrospinal fluid management module to perform a treatment on cerebrospinal fluid of the patient when the value related to the monitored measurements of the one or more physiological parameters reaches or goes beyond the threshold value.

Alternatively or additionally to any of the embodiments above, wherein the treatment on cerebrospinal fluid of the patient is a predetermined treatment based on a type of physiological parameter associated with the monitored measurements.

Alternatively or additionally to any of the embodiments above, wherein the treatment on cerebrospinal fluid of the patient is a predetermined treatment based on the comparison of the value related to the monitored measurements of the one or more physiological parameters and a type of physiological parameter associated with the monitored measurements.

Alternatively or additionally to any of the embodiments above, wherein the value related to the monitored measurements of the one or more physiological parameters is an indexed value related to measurements of two or more physiological parameters of the patient.

Alternatively or additionally to any of the embodiments above, wherein the indexed value is a value of an index based on measurements of the two or more physiological parameters of the patient.

Alternatively or additionally to any of the embodiments above, wherein the indexed value is a value of an index based on two or more of sub-indices and each sub-index of the two or more of sub-indices is based on measurements of two or more physiological parameters of the patient.

Alternatively or additionally to any of the embodiments above, wherein the value related to the monitored measurements of the one or more physiological parameters is a value of a measurement of a physiological parameter of the one or more physiological parameters.

Alternatively or additionally to any of the embodiments above, wherein the one or more physiological parameters include one or more physiological parameters selected from a group consisting of intracranial pressure, cerebral pressure perfusion, mean arterial pressure, heart rate, brain oxygenation, cerebral blood flow, and a cytokine level.

Alternatively or additionally to any of the embodiments above, wherein the cerebrospinal fluid management module comprises a cooling treatment module.

Alternatively or additionally to any of the embodiments above, wherein the cerebrospinal fluid management module comprises a filtration treatment module.

Alternatively or additionally to any of the embodiments above, wherein the cerebrospinal fluid management module comprises a cooling treatment module and a filtration treatment module.

Alternatively or additionally to any of the embodiments above, wherein the cerebrospinal fluid management module comprises a circulation module having a pump configured to pump cerebrospinal fluid from the patient to a treatment module.

Alternatively or additionally to any of the embodiments above, further comprising: a communications port in communication with the controller; and wherein the communications port is configured to receive the measurements of the one or more physiological parameters of a patient that are monitored by the controller.

Alternatively or additionally to any of the embodiments above, further comprising: a communications port in communication with the controller; and wherein the communications port is configured to facilitate communication between the cerebrospinal fluid management module and the controller.

Alternatively or additionally to any of the embodiments above, further comprising: a wireless communications port in communication with the controller and configured to facilitate communication between the controller and a device over a wireless network.

Alternatively or additionally to any of the embodiments above, further comprising: a user interface in communication with the controller; and wherein the user interface is configured to receive inputs that modify an operation of the controller.

Alternatively or additionally to any of the embodiments above, wherein the user interface is configured to display a medical image of the patient in a selectable pane and one or both of the measurements of the one or more physiological parameters of a patient and the value related to the monitored measurements of the one or more physiological parameters in a real-time updating pane position on the user interface adjacent the selectable pane.

Another example includes a cerebrospinal fluid circulation system. The system comprising: a controller; a circulation management module in communication with the controller; a cerebrospinal fluid treatment management module in communication with the controller; wherein the controller is configured to automatically control the circulation management module and the cerebrospinal fluid treatment management module based on measurements of one or more physiological parameters of a patient.

Alternatively or additionally to any of the embodiments above, wherein the controller is configured to control the circulation management module to maintain a predetermined cerebrospinal fluid flow rate.

Alternatively or additionally to any of the embodiments above, wherein the controller is configured to control the circulation management module to maintain a cerebrospinal fluid pressure at or below a set point level.

Alternatively or additionally to any of the embodiments above, wherein the cerebrospinal fluid management treatment module is configured to include one or more exchangeable treatment modules.

Alternatively or additionally to any of the embodiments above, wherein the one or more exchangeable treatment modules include one or more treatment modules selected from a group consisting of a cooling treatment module and a filtration treatment module.

Alternatively or additionally to any of the embodiments above, wherein the cerebrospinal fluid treatment management module includes a cooling treatment module.

Alternatively or additionally to any of the embodiments above, wherein the controller is configured such that when the controller determines a value related to a measurement of a physiological parameter of a patient reaches or goes beyond a threshold value, the controller adjusts operation the circulation management module to actively drain cerebrospinal fluid while adjusting operation of the cooling treatment module to cool cerebrospinal fluid for a predetermined time period.

Alternatively or additionally to any of the embodiments above, wherein the cerebrospinal fluid treatment management module includes a filtration treatment module.

Alternatively or additionally to any of the embodiments above, wherein the controller is configured such that when the controller determines a value related to a measurement of a physiological parameter of a patient reaches or goes beyond a threshold value, the controller adjusts operation of the circulation management module to circulate cerebrospinal fluid at a predetermined rate while adjusting operation of the filtration treatment module to filter a contaminant from cerebrospinal fluid.

Another example includes a method of managing inflammation. The method comprising: monitoring measurements of one or more physiological parameters of a patient over time; comparing a value related to the monitored measurements of the one or more physiological parameters to a threshold value; and adjusting operation of a cerebrospinal fluid management module based on the comparison of the value related to the monitored measurements of the one or more physiological parameters to the threshold value.

Alternatively or additionally to any of the embodiments above-further comprising: determining a difference between the value related to the monitored measurements of the one or more physiological parameters and the threshold value; and wherein the adjusting operation of the cerebrospinal fluid management module is based on the determined difference between the value related to the monitored measurements of the one or more physiological parameters and the threshold value.

Alternatively or additionally to any of the embodiments above, wherein the adjusting operation of the cerebrospinal fluid management module is automatically initiated based on the comparison of the value related to the monitored measurements of the one or more physiological parameters to the threshold value.

Alternatively or additionally to any of the embodiments above, wherein the adjusting operation of a cerebrospinal fluid management module initiates a treatment start protocol in response to the value related to the monitored measurements of the one or more physiological parameters reaching or going beyond the threshold value a first time.

Alternatively or additionally to any of the embodiments above, wherein the adjusting operation of a cerebrospinal fluid management module initiates a treatment stop protocol in response to the value related to the monitored measurements of the one or more physiological parameters reaching or going beyond the threshold value a second time after reaching or going beyond the threshold value the first time.

Alternatively or additionally to any of the embodiments above, wherein the adjusting operation of a cerebrospinal fluid management module initiates a treatment stop protocol in response to the value related to the monitored measurements of the one or more physiological parameters reaching or going beyond the threshold value.

Alternatively or additionally to any of the embodiments above, wherein the adjusting operation of a cerebrospinal fluid management module initiates a predetermined treatment protocol based on a type of physiological parameter associated with the monitored measurements.

Alternatively or additionally to any of the embodiments above, wherein the adjusting operation of a cerebrospinal fluid management module initiates a predetermined treatment protocol based on the comparison of the value related to the monitored measurements of the one or more physiological parameters to the threshold value and a type of physiological parameter associated with the monitored measurements.

Alternatively or additionally to any of the embodiments above, wherein the adjusting operation of a cerebrospinal fluid management module causes the cerebrospinal fluid management module to initiate a cooling treatment protocol.

Alternatively or additionally to any of the embodiments above, wherein the adjusting operation of a cerebrospinal fluid management module causes the cerebrospinal fluid management module to initiate a filtration treatment protocol.

Alternatively or additionally to any of the embodiments above, wherein the adjusting operation of a cerebrospinal fluid management module causes the cerebrospinal fluid management module to initiate a filtration treatment protocol and a cooling treatment protocol.

Another example includes a computer readable medium having stored thereon in a non-transitory state a program code for use by a computing device, the program code causing the computing device to execute a method for managing inflammation, the method comprising: determining a value related to one or more measurements of one or more physiological parameters; comparing the value related to the one or more measurements of the one or more physiological parameters to a threshold value; and outputting a control signal to adjust operation of a cerebrospinal fluid management module based on the comparison of the value related to the one or more measurements of the one or more physiological parameters to the threshold value.

Alternatively or additionally to any of the embodiments above, the method further comprising: determining a difference between the value related to the one or more measurements of the one or more physiological parameters and the threshold value; wherein the control signal adjusting operation of the cerebrospinal fluid management module is based on the determined difference between the value related to the one or more measurements of the one or more physiological parameters and the threshold value.

Alternatively or additionally to any of the embodiments above, wherein the outputting of the control signal is automatically initiated based on the comparison of the value related to the one or more measurements of the one or more physiological parameters to the threshold value.

Alternatively or additionally to any of the embodiments above, wherein the outputted control signal adjusting operation of a cerebrospinal fluid management module is configured to initiate a treatment start protocol in response to the value related to the one or more measurements of the one or more physiological parameters reaching or going beyond the threshold value a first time.

Alternatively or additionally to any of the embodiments above, wherein the outputted control signal adjusting operation of a cerebrospinal fluid management module is configured to initiate a treatment stop protocol in response to the value related to the one or more measurements of the one or more physiological parameters reaching or going beyond the threshold value a second time after reaching or going beyond the threshold value the first time.

Alternatively or additionally to any of the embodiments above, wherein the outputted control signal adjusting operation of a cerebrospinal fluid management module is configured to initiate a treatment stop protocol in response to the value related to the one or more measurements of the one or more physiological parameters reaching or going beyond the threshold value.

Alternatively or additionally to any of the embodiments above, wherein the outputted control signal adjusting operation of a cerebrospinal fluid management module is configured to initiate a predetermined treatment protocol based on a type of physiological parameter associated with the one or more measurements.

Alternatively or additionally to any of the embodiments above, wherein the outputted control signal adjusting operation of a cerebrospinal fluid management module is configured to initiate a predetermined treatment protocol based on the comparison of the value related to the one or more measurements of the one or more physiological parameters to the threshold value and a type of physiological parameter associated with the one or more measurements.

Alternatively or additionally to any of the embodiments above, wherein the outputted control signal adjusting operation of a cerebrospinal fluid management module causes a cerebrospinal fluid management module to initiate a cooling treatment protocol.

Alternatively or additionally to any of the embodiments above, wherein the outputted control signal adjusting operation of a cerebrospinal fluid management module causes a cerebrospinal fluid management module to initiate a filtration treatment protocol.

Alternatively or additionally to any of the embodiments above, wherein the outputted control signal adjusting operation of a cerebrospinal fluid management module causes a cerebrospinal fluid management module to initiate a filtration treatment protocol and a cooling treatment protocol.

Another example includes an inflammation management system for managing a patient condition based on values of physiological parameters of a patient. The inflammation system may include a port configured to communicate with one or more input devices, the port may be configured to receive values related to one or more physiological parameters of a patient from the one or more input devices; memory for storing received values related to the one or more physiological parameters of the patient; a processor operatively coupled to the port and the memory, the processor may be configured to process the received values related to the one or more physiological parameters of the patient and identify when an inflammation condition of the patient reaches a treatment condition based on the processed received values related to the one or more physiological parameters of the patient; and wherein the processor wherein configured to output, via the port, one or more indications that establish the inflammation condition of the patient has reached the treatment condition.

Alternatively or additionally to any of the embodiments above, wherein the processor may be configured to output a control signal to a cerebrospinal fluid management module to perform a treatment on cerebrospinal fluid of the patient in response to identifying when the inflammation condition of the patient reaches the treatment condition.

Alternatively or additionally to any of the embodiments above, the inflammation management system may further comprise: a user interface in communication with the processor via the port; and wherein the processor may be configured to display a suggested treatment protocol on the user interface in response to identifying the inflammation condition of the patient reaches the treatment condition.

Alternatively or additionally to any of the embodiments above, wherein the processor may be configured to determine an indexed value based on the received values related to the one or more physiological parameters and identify when the inflammation condition of the patient reaches the treatment condition based on the indexed value.

Alternatively or additionally to any of the embodiments above, wherein the received values may relate to two or more physiological parameters and the indexed value may be determined based on the received values for at least two physiological parameters.

Alternatively or additionally to any of the embodiments above, wherein the indexed value may be a value of a brain inflammation index and the values for the at least two physiological parameters may comprise a value for white blood cell count (WBC), a value for body temperature, a value for heart rate variability, and a value for photoplethysmography.

Alternatively or additionally to any of the embodiments above, wherein the indexed value may be a value of a mass effect index and the values for the at least two physiological parameters may include a value for a midline shift from a CT scan, a value for blood volume, a value for edema volume, a value for intracranial pressure, a value for water in a brain of the patient, and a value for brain tissue.

Alternatively or additionally to any of the embodiments above, wherein the indexed value may be a value of a National Institute of Health Stroke Scale index and the values for the at least two physiological parameters may include a value for a level of consciousness, a value of eye measurements with a pupilometer, a value of motor skills, a value of sensations, and a value of language skills.

Alternatively or additionally to any of the embodiments above, wherein the indexed value may be a value of a fluid management index and the values for the at least two physiological parameters may include a value for a blood pressure, a value for a fluid input and output, a value for cerebral perfusion pressure, a value for sodium content, and a value for potassium content.

Alternatively or additionally to any of the embodiments above, wherein the indexed value may be a value of a Glasgow Coma Scale index and the values for the at least two physiological parameters may include a value of eye measurements, a value of motor skills, and a value of language skills.

Alternatively or additionally to any of the embodiments above, wherein the indexed value may be based on a plurality of sub-index values.

Alternatively or additionally to any of the embodiments above, wherein the plurality of sub-index values may include values of two or more of a value of an inflammation index, a value of a mass effect index, a value of a National Institute of Health Stroke Scale index, a value of a fluid management index, and value of a Glasgow Coma Scale index.

Alternatively or additionally to any of the embodiments above, wherein the treatment condition may be a condition related to a subarachnoid hemorrhage of the patient and the indexed value may be based on a value of an inflammation index, a value of a mass effect index, a value of a National Institute of Health Stroke Scale index, and a value of a fluid management index.

Alternatively or additionally to any of the embodiments above, wherein the treatment condition may be a condition related to an intracranial hemorrhage of the patient and the indexed value may be based on a value of an inflammation index, a value of a mass effect index, and a value of a National Institute of Health Stroke Scale index.

Alternatively or additionally to any of the embodiments above, wherein the treatment condition is a condition related to a traumatic brain injury of the patient and the indexed value is based on a value of an inflammation index, a value of a mass effect index, and a value of a Glasgow Coma Scale index.

Alternatively or additionally to any of the embodiments above, wherein the indexed value may be indicative of a trend for the inflammation condition of the patient over time.

Another example includes a method of managing inflammation to treat a patient condition, the method comprising: receiving values related to physiological parameters of a patient; with a processor, processing the values related to one or more physiological parameters of the patient; with the processor, identifying an inflammation condition of the patient has reached a treatment condition based on the processed values related to the one or more physiological parameters of the patient; and in response to identifying the inflammation condition of the patient has reached the treatment condition, automatically outputting via a port in communication with the processor an indication that the inflammation condition of the patient has reached the treatment condition.

Alternatively or additionally to any of the embodiments above, wherein outputting the indication that the inflammation condition of the patient has reached the treatment condition may comprises: outputting a control signal from the processor to a cerebrospinal fluid management module instructing the cerebrospinal fluid management module to perform a treatment on cerebrospinal fluid of the patient.

Alternatively or additionally to any of the embodiments above, the method may further comprise: automatically selecting the treatment for treating the cerebrospinal fluid of the patient with the processor based on the processed values related to the physiological parameters of the patient.

Alternatively or additionally to any of the embodiments above, wherein outputting the indication that the inflammation condition of the patient has reached the treatment condition may comprise: displaying on a user interface a suggested treatment protocol for treatment of the inflammation condition.

Alternatively or additionally to any of the embodiments above, the method may further comprise: in response to identifying the inflammation condition of the patient has reached the treatment condition, automatically selecting the suggested treatment protocol from a treatment protocol module with the processor based on the processed values related to the one or more physiological parameters of the patient.

Alternatively or additionally to any of the embodiments above, wherein: processing the values related to the one or more physiological parameters of the patient may comprise determining an indexed value based on the values related to the one or more physiological parameters of the patient; and identifying the inflammation condition of the patient has reached the treatment condition may be based on the indexed value.

Alternatively or additionally to any of the embodiments above, wherein: the values related to the one or more physiological parameters of the patient that are received may relate to two or more physiological parameters of the patient; and the indexed value may be determined based on values for at least two physiological parameters.

Alternatively or additionally to any of the embodiments above, wherein the indexed value may be a value of a brain inflammation index and the values for the at least two physiological parameters may comprise a value for white blood cell count (WBC), a value for body temperature, a value for heart rate variability, and a value for photoplethysmography.

Alternatively or additionally to any of the embodiments above, wherein the indexed value may be a value of a mass effect index and the values for the at least two physiological parameters may include a value for midline shift from a CT scan, a value for blood volume, a value for edema volume, a value for intracranial pressure, a value for water in a brain of the patient, and a value for brain tissue.

Alternatively or additionally to any of the embodiments above, wherein the indexed value may be a value of a National Institute of Health Stroke Scale index and the values for the at least two physiological parameters may include a value for a level of consciousness, a value of eye measurements, a value of motor skills, a value of sensations, and a value of language skills.

Alternatively or additionally to any of the embodiments above, wherein the indexed value may be a value of a fluid management index and the values for the at least two physiological parameters may include a value for a blood pressure, a value for a fluid input and output, a value for cerebral perfusion pressure, a value for sodium content, and a value for potassium content.

Alternatively or additionally to any of the embodiments above, wherein the indexed value may be a value of a Glasgow Coma Scale index and the values for the at least two physiological parameters may include a value of eye measurements, a value of motor skills, and a value of language skills.

Alternatively or additionally to any of the embodiments above, wherein determining the indexed value may comprise processing a plurality of sub-index values.

Alternatively or additionally to any of the embodiments above, wherein the plurality of sub-index values may include values of two or more of a value of an inflammation index, a value of a mass effect index, a value of a National Institute of Health Stroke Scale index, a value of a fluid management index, and a value of a Glasgow Coma Scale index.

Alternatively or additionally to any of the embodiments above, wherein the treatment condition may be a condition related to a subarachnoid hemorrhage of the patient and the indexed value may be based on a value of an inflammation index, a value of a mass effect index, a value of a National Institute of Health Stroke Scale index, and a value of a fluid management index.

Alternatively or additionally to any of the embodiments above, wherein the treatment condition may be a condition related to an intracranial hemorrhage of the patient and the indexed value may be based on a value of an inflammation index, a value of a mass effect index, and a value of a National Institute of Health Stroke Scale index.

Alternatively or additionally to any of the embodiments above, wherein the treatment condition may be a condition related to a traumatic brain injury of the patient and the indexed value may be based on a value of an inflammation index, a value of a mass effect index, and a value of a Glasgow Coma Scale index.

Another example includes a computer readable medium having stored thereon in a non-transitory state a program code for use by a computing device, the program code causing the computing device to execute a method for managing inflammation to treat a patient condition comprising: storing values related to one or more physiological parameters of a patient in memory; determining an indexed value based on the values related to the one or more physiological parameters of the patient stored in the memory; identifying an inflammation condition of the patient has reached a treatment condition based on the indexed value; and in response to identifying the inflammation condition of the patient has reached the treatment condition, automatically outputting an indication that the inflammation condition of the patient has reached the treatment condition.

Alternatively or additionally to any of the embodiments above, wherein automatically outputting the indication that the inflammation condition of the patient has reached the treatment condition may comprise outputting a control signal to a cerebrospinal fluid management module instructing the cerebrospinal fluid management module to perform a treatment protocol on cerebrospinal fluid of the patient.

Alternatively or additionally to any of the embodiments above, wherein the method may further comprise: automatically selecting the treatment protocol for treating the cerebrospinal fluid of the patient based on the indexed value.

Alternatively or additionally to any of the embodiments above, wherein automatically outputting the indication that the inflammation condition of the patient has reached the treatment condition may comprise displaying on a user interface a suggested treatment protocol for treatment of the inflammation condition.

Alternatively or additionally to any of the embodiments above, wherein the method may further comprise: in response to identifying the inflammation condition of the patient has reached the treatment condition, automatically selecting the suggested treatment protocol for treatment of the inflammation condition based on the indexed value.

Alternatively or additionally to any of the embodiments above, wherein determining the indexed value may comprise processing a plurality of sub-index values.

Alternatively or additionally to any of the embodiments above, where the plurality of sub-index values may include values of two or more of a value of an inflammation index, a value of a mass effect index, a value of a National Institute of Health Stroke Scale index, a value of a fluid management index, and value of a Glasgow Coma Scale index.

Alternatively or additionally to any of the embodiments above, wherein the indexed value may be indicative of a trend for the inflammation condition of the patient over time.

Another example includes an inflammation management system for managing a patient condition based on values of physiological parameters of a patient, the system may comprise: a port configured to communicate with one or more input devices, the port is configured to receive values related to physiological parameters of a patient from the one or more input devices; memory for storing received values related to the physiological parameters of the patient; a processor operatively coupled to the port and the memory, the processor may be configured to process the received values related to the physiological parameters of the patient and establish an indexed value indicative of a trend for an inflammation condition of the patient over time based on the received values related to the physiological parameters; and wherein the processor may be configured to output, via the port, an indication based on the indexed value.

Alternatively or additionally to any of the embodiments above, wherein the indication based on the indexed value may comprise an indication that establishes the inflammation condition of the patient has reached a treatment condition.

Alternatively or additionally to any of the embodiments above, wherein the indication based on the indexed value may comprise a control signal to a cerebrospinal fluid management module to perform a treatment on cerebrospinal fluid of the patient in response to the inflammation condition of the patient reaching the treatment condition.

Alternatively or additionally to any of the embodiments above, may further comprise: a user interface in communication with the processor via the port, the user interface may include a first pane displaying values related to the physiological parameters of the patient over time and a second pane; and wherein the indication based on the indexed value may comprises a control signal from the processor to the user interface to display the indexed value in the first pane.

Alternatively or additionally to any of the embodiments above, wherein the indexed value may be displayed in the first pane relative to a range of possible indexed values and the values related to the physiological parameters of the patient may be displayed in the second pane relative to a predetermined time period.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
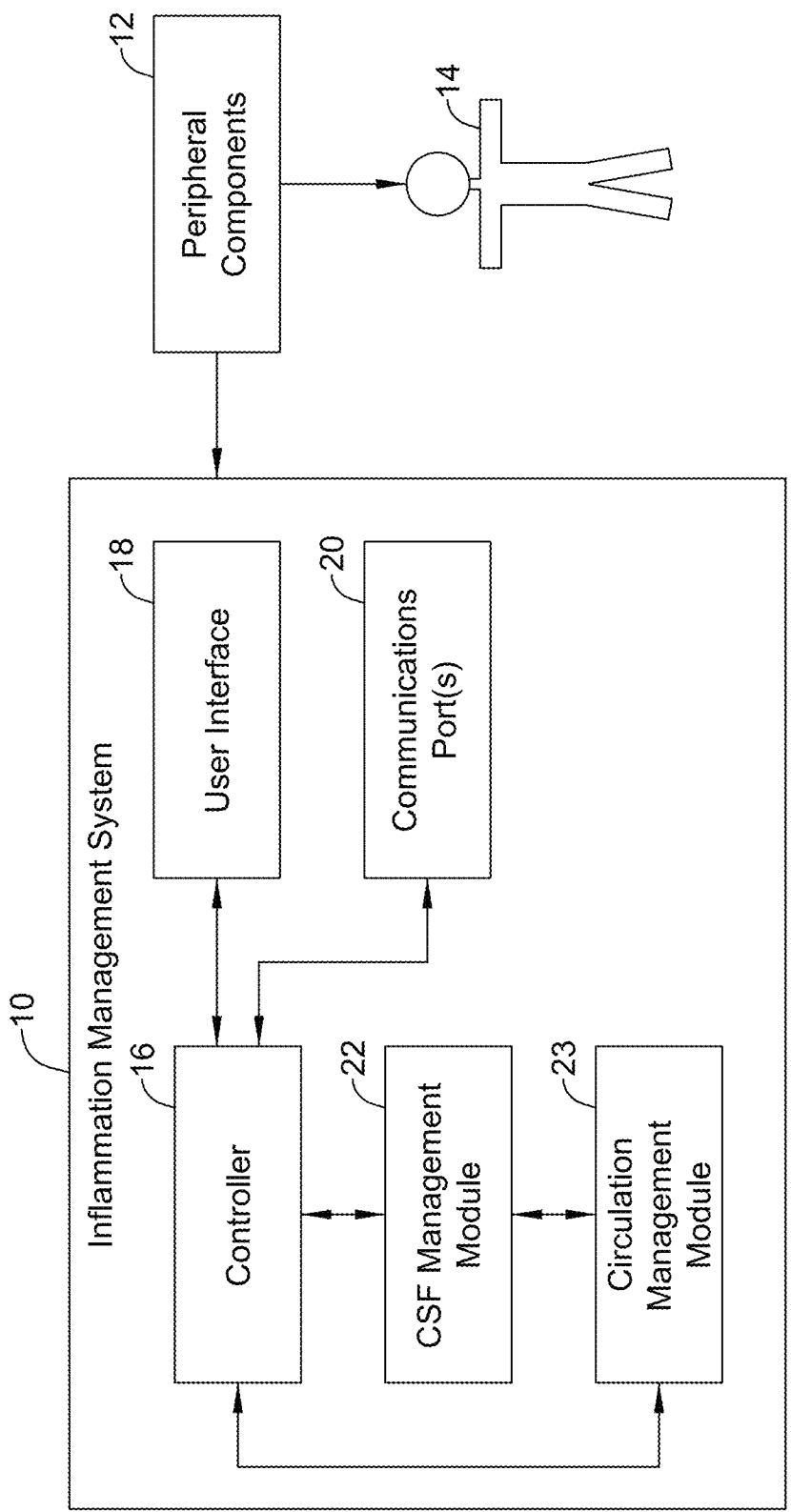
FIG. 1 is a schematic depiction of an example inflammation management system in communication with a patient.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAIL DESCRIPTION

The incidence of stroke, intracranial hemorrhage, traumatic brain injury (TBI) and subarachnoid hemorrhage result in over 1.1 million hospital admissions per year. Acute Ischemic Stroke alone accounts for 700,000 admissions per year. Acute brain injury (e.g., caused by trauma, hemorrhage, stroke, etc.) may occur in various degrees and may require that the brain go through a healing process.

A patient with an injured brain may deal with fever, seizures, swelling, and/or high intracranial pressure. As discussed below, physicians today have limited tools at their disposal to assist in the diagnosing, treating and healing of brain injuries.

Between one-quarter and more than one-half of patients admitted to the neurological intensive care unit (NICU) for acute brain injury develop a fever. The cause of fever in these patients often remains unexplained. Central fever related to loss of the physiological regulation of body temperature by the hypothalamus is often proposed as a possible cause for persistent fever in patients with acute brain injuries that have no evidence of infection. As hyperthermia is strongly detrimental for the recovery of an acutely injured brain and contributes to an increase in the length of stay in the NICU, techniques to restore body temperature to a normal "operating" temperature (e.g., ~98.6 degrees Fahrenheit (F)) play an important role in minimizing inflammation and restoring healing to an injured brain.

Status epilepticus (SE), a condition in which epileptic seizures follow one another without recovery of consciousness between the seizures, affects up to 150,000 patients each year in the United States, with a mortality between 3% and 33%. Initial treatment of SE with drugs (e.g., benzodiazepines, phenytoin, and/or phenobarbital) typically fails to terminate SE in 30%-50% of SE cases. The lack of curing SE after treatment with drugs may be particularly problematic because cases of longer duration become more difficult to treat. Even infusions of anesthetics (e.g., doses of midazolam, pentobarbital, and propofol) that are traditionally used to control refractory SE, fail in 8%-21% of cases. Furthermore, seizures, particularly prolonged seizures or seizure episodes, pose a risk of permanent neuronal damage. Given the incomplete efficacy of current therapies and the potential for neurologic damage, improved diagnoses and earlier treatments need to treat and reduce brain injuries in patient that have SE.

Effective cerebral oxygenation requires an adequate cerebral perfusion pressure and patients suffering an acute brain injury and/or other conditions may be susceptible to inadequate cerebral perfusion pressures. Cerebral perfusion pressure may depend upon the 'resistance' offered by intracranial pressure (ICP) or jugular venous pressure (JVP), whichever is higher. Intracranial pressure is determined by the relative proportion of soft tissue, blood, and CSF within the cranium. In healthy, supine adults normal ICP is 5-15 mmHg, becoming sub-atmospheric on standing (around -10 mmHg). Sustained elevations in ICP have been shown to adversely affect patient outcomes and as such, intracranial hypertension (i.e., elevated ICP) provides a modifiable risk factor in the management of patients with an acute brain injury or other head injuries. In most cases, relatively conservative methods such as head elevation, sedation, and/or osmotherapy are sufficient for treating lower ICP. In over 50,000 cases annually, however, ICP remains elevated despite the use of these conservative treatment methods.

The disclosed concepts may provide an inflammation management system that may diagnose and/or administer therapy in a manner configured to improve outcomes for patients with acute brain injury. For example, the inflammation management system may be configured to, or may be configured to facilitate, an early diagnosis of a condition related to an acute brain injury or other head condition and/or treat the condition related to the acute brain injury or other head condition. In some cases, the inflammation management system may be configured to treat diagnoses of a patient by conditioning cerebral spinal fluid of the patient.

Cerebrospinal fluid (CSF) is a generally clear, colorless fluid that is produced in the ventricles, specifically the choroid plexuses, in the brain. The choroid plexus produces approximately 500 milliliters of CSF daily in order to accommodate flushing or recycling of CSF to remove toxins and metabolites, which happens several times per day. From the choroid plexus, CSF flows slowly through a channel (canal) into the space surrounding the brain and spinal column, and then into the body. CSF is found in the space between the pia mater and the arachnoid mater, known as the subarachnoid space. CSF is also found in and around the ventricular system in the brain, which is continuous with the central canal of the spinal cord. In the event of an acute brain injury (e.g., a stroke or other brain trauma) or other head injury, it can be desirable to remove the CSF from one location (e.g., the cervical region of the spine, or a brain ventricle), treat (e.g., condition) the removed CSF, and return the removed CSF to the CSF space at the one location and/or at a second location (e.g., the lumbar region of the spine).

Conditioning therapies, such as Neurapheresis™ therapy and/or other suitable conditioning therapies, may result in the removal of materials (e.g., microorganisms, cells, viruses, foreign material, drugs, combinations thereof, and the like) from CSF. In addition or as an alternative to being used to treat conditions related to acute brain injuries (e.g., stroke, TBI, encephalitis, etc.) and/or conditions related to other head injuries, these conditioning therapies and other therapeutic techniques may be used to treat a number of other neurological diseases or conditions, such as Alzheimer's Disease, Parkinson's Disease, Huntington's Disease, Amyotrophic Lateral Sclerosis (ALS), Meningitis from various causes, Guillain-Barré Syndrome (GBS), Multiple Sclerosis (MS), HIV-associated neurocognitive disorders, Spinal Cord Injury, cerebral vasospasm, and other diseases or conditions.

Purification, conditioning, and/or compound removal schema or systems are be adjustable to a broad range of physiological parameters and flows. For example, the schema and/or systems can be tailored to a specific disease or group of diseases as suitable, including based on a number of features of the disease(s), such as size, affinity, biochemical properties, temperature, and/or other features. Purification schema may be based on diffusion, size-exclusion, ex-vivo immunotherapy using immobilized antibodies or antibody fragments, hydrophobic/hydrophilic, anionic/cationic, high/low binding affinity, chelators, anti-bacterial, anti-viral, anti-DNA/RNA/amino acid, enzymatic, and magnetic and/or nanoparticle-based systems.

With regard to an inflammation management system for monitoring a patient (e.g., monitoring a condition of the patient) and/or for use in CSF conditioning therapies (e.g., Neurapheresis™ therapy and/or other conditioning therapies), the disclosed inflammation management system can be used to safely and quickly access the CSF space with minimal disturbance to the CSF flow in response to diagnosing a condition of a patient. The systems and devices disclosed herein provide a safe and rapid flow circuit.

The inflammation management systems and related devices disclosed herein may be used to access the CSF space to remove the CSF from one location (e.g., the cervical region of the spine, or a brain ventricle), condition or otherwise treat the removed CSF, and return the conditioned CSF to the CSF space, including at a second location (e.g., the lumbar region of the spine), safely and efficiently. In various aspects, the inflammation management system and related devices disclosed herein may maintain the endogenous ICP or intraspinal pressure within a physiological range, for example, from about 5 to about 20 mm Hg or from about 0 to about 10 mm Hg or from about −5 to about 10 mm Hg or from about −5 to about 25 mm Hg.

In various aspects, the inflammation management system and related devices disclosed herein may reduce or eliminate recirculating flow loops, which may improve an efficiency of the inflammation management system. In some aspects, the inflammation management system may include sensors within a catheter or within the flow circuit to detect clogs or blockages in the system, thereby providing closed loop pressure control.

In certain aspects, the inlet-outlet spacing of the inflammation management system may be selected to be maximized while staying below the level of a cervical region of a patient. Additionally or alternatively, the inflammation management system and related devices may maintain spacing between the inlet and outlet, for example, within a range from about 10 cm to about 40 cm. In certain implementations, the spacing is within a range from about 10 cm to about 30 cm.

In certain aspects, the inlet-outlet spacing may be selected based on vertebral spacing. For example, the spacing may be selected so that the inlet-outlet spacing is within a range of lengths from approximately five (5) vertebrae to approximately twelve (12) vertebrae. In certain implementations, a spacing of approximately 10 vertebrae may be selected; however, other configurations (such as those described elsewhere in the specification) may be utilized. When designing such spacing, it may be assumed that a vertebra is approximately 2-3 cm in length, however, other measurements and designs may be used.

In certain implementations, a particular size, shape, and/or other configuration of a lumen of a catheter for use with the inflammation management system may be selected to facilitate a catheter unblocking and/or the ability of the catheter to resist blockage. For example, a proximal outer diameter of a lumen within a range from approximately 0.060 inches to approximately 0.070 inches and a proximal inner diameter within a range from approximately 0.025 inches to approximately 0.060 inches may be selected; however, other configurations (such as those described elsewhere in the specification) may be utilized. In some aspects, there may also be multiple holes along an inlet and/or outlet of the catheter for redundancy in case there is tissue blocking some number of holes. In certain implementations, a particular coil pitch of a coiled wire within the catheter may be selected in order to reduce kinking of the catheter.

The disclosed inflammation management systems and related devices may be used to access the CSF space and may be used at any access point in the cervical (C1-C7), thoracic (T1-T12), or lumbar region (L1-L5) of the vertebral column. An access site in the cervical region may be used to access the ventricular system in the brain. In one embodiment, the system and device are used to access the lumbar region. In some embodiments, the inlets and outlets of the inflammation management system may be located in places along the spine such that the drainage process will not cause tissue to be drawn into the catheter. For example, when a patient is lying on a table, entry may be made at a suitable angle, such as, for example, about 90 degrees, to access the spine. A traditional catheter must be pushed through a 90 degree bend at the L4-L6 region. Components (e.g., catheters and related delivery and/or other peripheral devices) of the inflammation management system disclosed herein may be curved such that they can access and navigate this angled bend more easily and efficiently.

Figure 2:
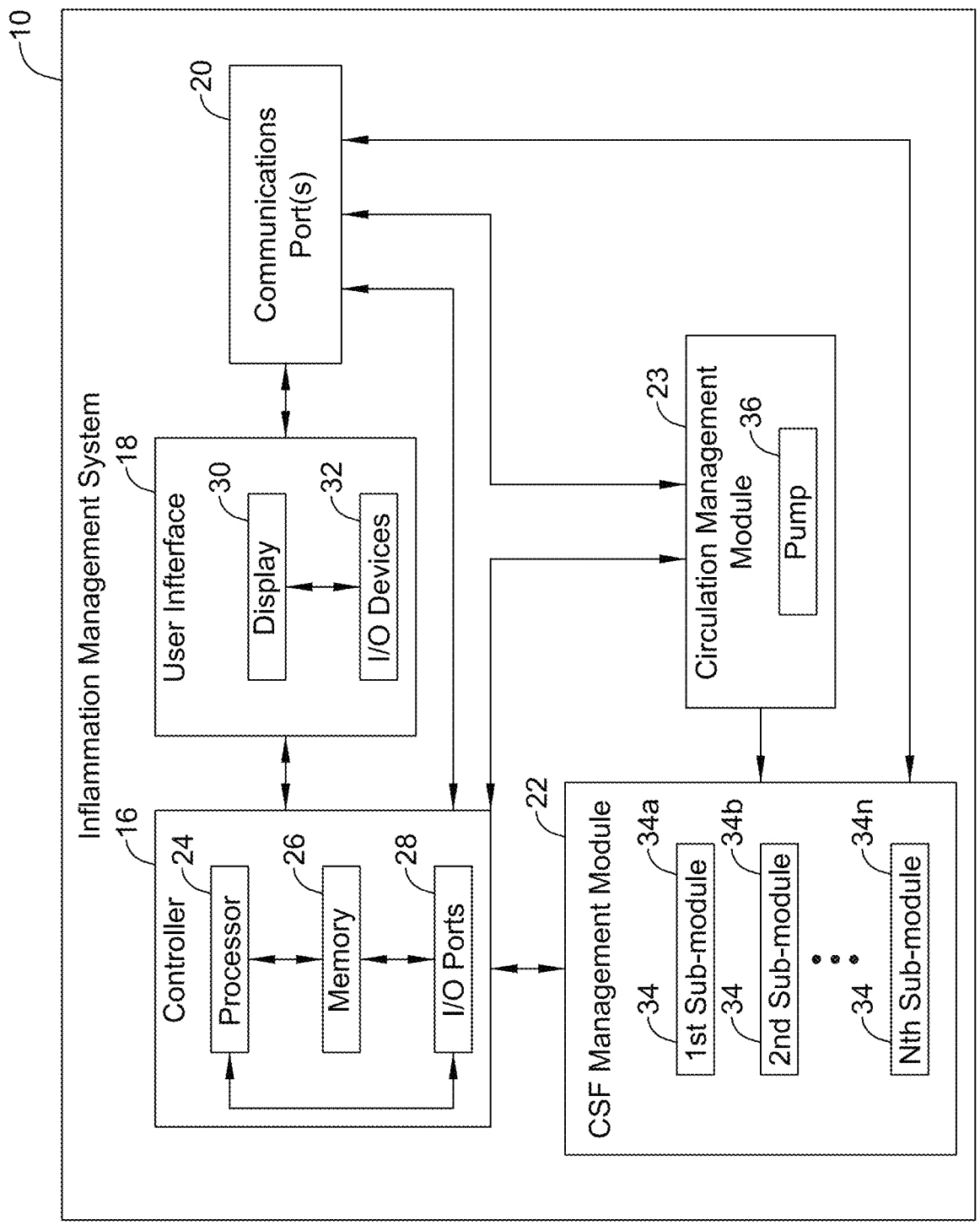
FIG. 2 is a schematic block diagram of an inflammation management system.
Figure 3:
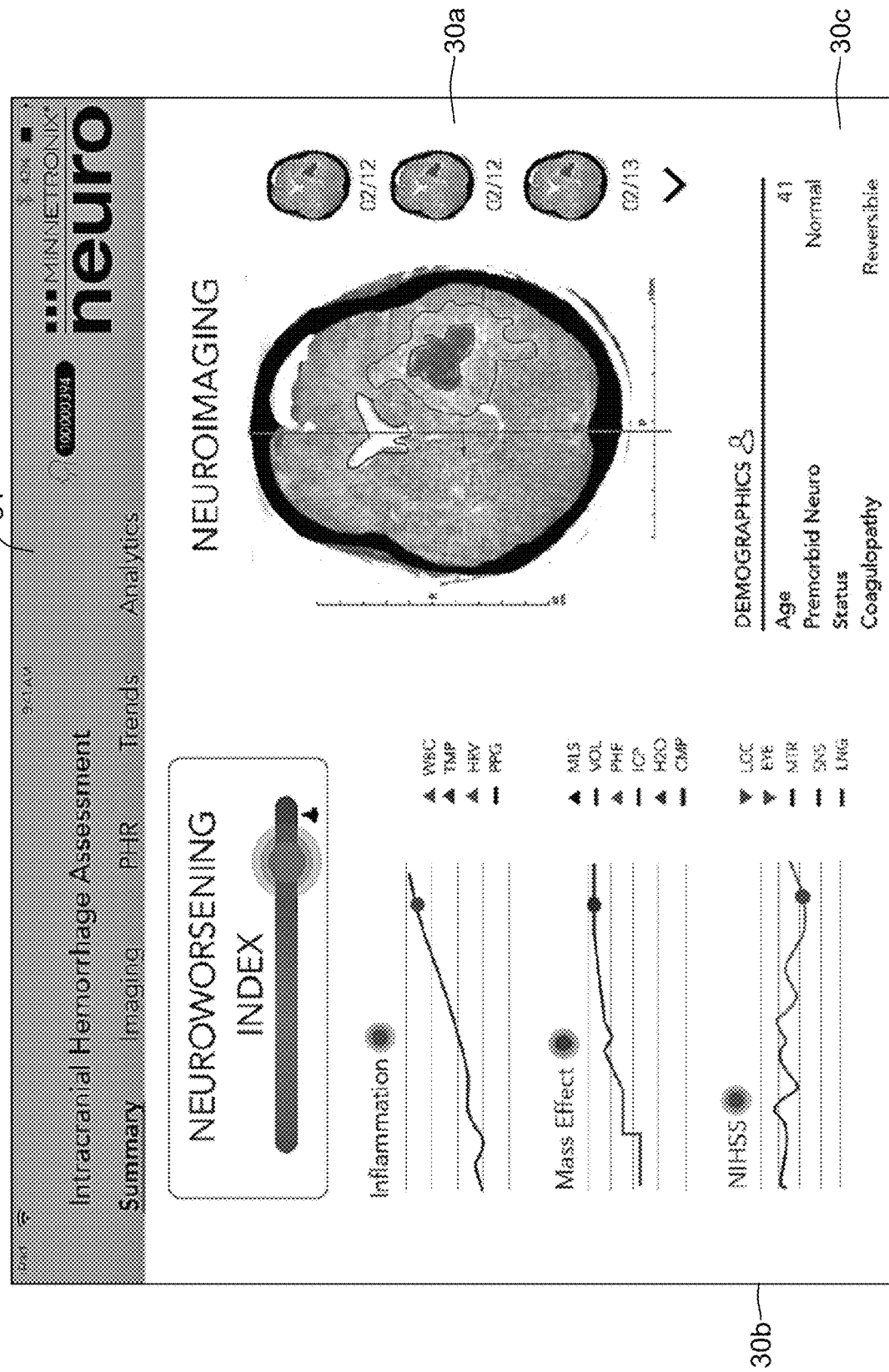
FIG. 3 is a schematic view of an example display of a user interface of an inflammation management system.

Turning to the Figures, FIG. 1 schematically depicts an inflammation management system 10 in communication with a patient 14. The inflammation management system 10 may include or may be configured to connect to one or more peripheral components 12 that are configured to be used in conjunction with the patient 14. In some cases, the inflammation management system 10 may include a controller 16, a user interface 18, one or more communications ports 20, a CSF management module 22 (e.g., a CSF treatment management module including a cooling module, a filtration module, and/or other suitable module), a circulation management module 23, and/or one or more other components suitable for use in operation of an inflammation management system 10. In some cases, although the circulation management module 23 may be separate from the controller 16 and the CSF management module 22, as depicted in FIGS. 1-3, part of or an entirety of the circulation management module 23 may be incorporated into one or both of the controller 16 and the CSF management module 22.

Each of the components of the inflammation management system 10 may be configured to communicate directly with one another. Alternatively, one or more of the components of the inflammation management system 10 may be configured to communicate with another component through the controller 16. For example, measurements from the peripheral components 12 may be received via the communications port(s) 20 and may be provided to the controller 16. The controller 16 then may interact with the CSF management module 22 to diagnose the patient and/or perform a treatment using the CSF management module 22. The controller 16 may interact with the circulation management module 23 to maintain a predetermined CSF flow rate and/or a CSF fluid pressure below a set point level and/or within a range of pressure levels.

The peripheral components 12 may include components used and/or configured to facilitate determining diagnoses of and applying therapy to the patient 14 using the inflammation management system 10. Example peripheral components 12 include, but are not limited to, catheters, sensors, electrical connectors, mechanical connectors, and/or other components configured to facilitate determining a diagnoses of the patient 14 and/or applying a therapy to the patient 14 using the inflammation management system 10.

The peripheral components 12 may include an implantable portion and/or an extracorporeal portion. In some cases, one or both of the implantable portion and the extracorporeal portion of the peripheral components 12 may have single use functionality and may be disposed after a use thereof, but this is not required.

The implantable portion may contain one or more sensors (e.g., constituent sensors, pressure sensors, temperature sensors, flow sensors, oxygen sensors, etc.) configured to sense measurements of one or more physiological parameters of the patient 14 that may be used by the inflammation management system 10 to control fluid temperature, pressure, and/or other suitable parameters. In one example, the implantable portion of the peripheral components 12 may include a temperature transducer and a pressure transducer that send signals to the inflammation management system 10 (e.g., to the controller 16 and/or the CSF management module 22. The implantable portion of the peripheral components 12 may be placed at one or more locations on the patient including, but not limited to between the skull and dura mater, between the dura mater and the brain, within a ventricle, in the subarachnoid space, and/or at one or more other suitable location. In some cases, the implantable portion may include a connector that extends to an exterior of a patient's body when implanted inside the body. Alternatively or in addition, the implantable portion may be connected to or coupled to the body of the patient without being implanted inside of the patient's body.

The extracorporeal portion may be a suitable component configured to connect to an input and/or an output of the inflammation management system 10 and connect to the implantable portion, such that the extracorporeal portion may act as an interface between the inflammation management system 10 and the implantable component. The extracorporeal portion of the peripheral components 12 may be and/or may include a sensor, a catheter, a tube, other elongated component, and/or other suitable component. Example sensors may be constituent sensors, pressure sensors, flow sensors, temperature sensors, oxygen sensors, and/or other suitable sensors configured to monitor fluid passing to and/or from the inflammation management system 10. Example catheters may be any suitable type of catheter configured to transfer fluid to and/or from the patient 14 to an inflammation management system 10. Example catheters that may be used with the inflammation management system 10 are described in U.S. Patent Application Ser. No. 62/286,413 filed on Jun. 18, 2018, and titled "SYSTEMS, CATHETERS, AND METHODS FOR TREATING ALONG THE CENTRAL NERVOUS SYSTEM", which is hereby incorporated by reference for all purposes. Other suitable catheters are contemplated.

FIG. 2 schematically depicts illustrative components of the inflammation management system 10. As discussed above with respect to FIG. 1, the inflammation management system 10 may include, among other components, the controller 16, the user interface 18, the communications ports 20, the CSF management module 22, and the circulation management module 23.

The controller 16 may include one or more components. In one example, the controller 16 may include a processor 24, memory 26 in communication with the processor 24, input/output (I/O) ports 28 in communication with the processor 24 and/or the memory 26, and/or one or more other suitable components. In some cases, the memory 26 may be or may include non-transitory computer readable medium that may include or may be programmed to include software and/or other instructions to be executed by the processor 24 and facilitate the controller 16 operating in an automated manner to output control signals via the I/O ports 28 to the CSF management module 22, to the circulation management module 23, to other components of the inflammation management system 10, and/or to other components usable with the inflammation management system 10 based on input received at the I/O ports 28 from the CSF management module 22, the user interface 18, and/or communications ports 20 communicating with peripheral components 12. Additionally or alternatively, the controller 16 may be configured to receive information from the CSF management module 22 and the circulation management module 23, and/or output control signals to the peripheral components via the communications ports 20, the user interface 18, and/or the communications ports 20.

The processor 24 may include a single processor or more than one processor working individually or with one another. Example processor components may include, but are not limited to microprocessors, microcontrollers, multi-core processors, graphical processing units, and/or other suitable processor components.

The memory 26 may include a single memory component or more than one memory component working individually or with one another. Example types of memory may include RAM, ROM, EEPROM, FLASH, other volatile or non-volatile memory, or other suitable memory for the controller 16.

The I/O ports 28 may be any type of communication port configured to communicate with the CSF management module 22, the circulation management module 23, the user interface 18, the communications ports 20, and/or one or more other components of the inflammation management system 10. Example I/O port types may include wired ports, wireless ports, radio frequency (RF) ports, Bluetooth ports, Near-Field Communication (NFC) ports, HDMI ports, Ethernet ports, VGA ports, serial ports, parallel ports, component video ports, S-video ports, composite audio/video ports, DVI ports, USB ports, optical ports, and/or other suitable ports. Although the I/O ports 28 are depicted as part of the controller 16 and separate from the communications port(s) 20, in additional and/or alternative instances, the I/O ports 28 may be at least part of the communications port(s) 20 and may be separate from the controller 16.

The user interface 18 may be any suitable type of user interface configured to facilitate a user interacting with the inflammation management system 10. For example, the user interface 18 may include a display 30, input/output (I/O) devices 32, and/or other suitable user interface components configured to facilitate a user interacting with the inflammation management system 10. The display 30 may include a touch screen and may be an LED, LCD, OLED or other display type. The I/O devices 32 may include and/or may be incorporated in or with one or more of a work station, a computer, a computing device, a tablet computer, a phone, a keypad, a display, a touch screen, a touch pad, a mouse, and/or one or more other suitable components that facilitate a user interacting with the inflammation management system 10.

As depicted in FIG. 3, the display 30 may include any suitable display configuration to facilitate displaying information relating to a patient that the inflammation management system 10 is monitoring and/or treating. In some cases, the display 30 may include one or more panes (e.g., where each pane may or may not be separated by visible boundaries). In one example, the display 30 may include a first pane 30*a* for displaying one or more medical images of the patient (e.g., an MRI, a CT scan, an x-ray, and/or other suitable medical image of the patient), a second pane 30*b* adjacent to the first pane 30*a* that displays measurements of, or values related to measurements of (e.g., which may be measurements of), and/or indicators related to measurements of one or more physiological parameters of the patient (e.g., intracranial hemorrhage (ICH) volume, brain inflammation, white blood cell count (WBC), body temperature (TMP), heart rate variability (HRV), photoplethysmography (PPG), mass effect on a brain, midline shift (MLS) from a CT scan, blood volume (VOL), edema volume (PHE), intracranial pressure (ICP), water in the brain, brain tissue compliance (CMP), National Institute of Health Stroke Scale (NIHSS), level of consciousness (LOC), eye measurements with a pupilometer, motor skills (MTR), sensations (SNS), language skills (LNG), fluid management, blood pressure (BP), fluid input and output (I/O), cerebral perfusion pressure (CPP), sodium content (Na++), potassium content (K++), and/or other suitable physiological parameters, an index of physiological parameters (e.g., inflammation index, Glasgow Coma Scale index, NIHSS index, mass effect index, a NEUROWORSENING™ index and/or other suitable indices), etc.), and a third pane 30*c* adjacent to the first pane 30*a* and/or the second pane 30*b* that displays patient information (e.g., information related to age, status, premorbid neuro, coagulopathy). The first pane 30*a*, the second pane 30*b*, and/or the third pane 30*c* may be updated in real time in response to incoming data and/or measurements as the data and/or measurements are received and/or updated at specified or predetermined intervals. Further, one or more of the first pane 30*a*, the second pane 30*b*, and the third pane 30*c* may be selectable and if selected, a pane with greater detail may be displayed on the display 30, a date range of the selected pane may be adjusted, and/or the controller 16 may cause one or more other suitable changes to what is being displayed on the display 30 and/or how a treatment is being applied.

Additionally or alternatively, the display 30 may include a header 31. The header 31 may be a pane with selectable options for selection to move between different displays (e.g., a Summary display, an Imaging display, a PHR display, a Trends display, an Analytics display, etc.)

The communications ports 20 may be separate from and/or part of other I/O ports (e.g., the I/O ports 28 and/or other suitable I/O ports) of the inflammation management system 10. The communications ports 20 may be one or more suitable types of communications ports configured to facilitate communication between the inflammation management system 10 and one or more other components configured to interact with the inflammation management system 10 (e.g., peripheral components 12, etc.). In one example, the communications ports 20 may be configured to connect to peripheral components 12 (e.g., to receive fluid from a patient and/or to receive measurements and/or data of one or more physiological parameters of a patient that may be monitored by the controller 16 where the measurements and/or data are received from sensors), connect to scanning equipment, connect to treatment components, and/or connect to other diagnostic components of and/or in communication with the inflammation management system 10.

In some instances, the communications ports 20 may be or may include mechanical communications ports and/or electrical communications ports. Example mechanical communications ports may include, but are not limited to, connection ports configured to facilitate a mechanical connection between the inflammation management system 10 and the peripheral components 12 and/or other suitable components. Such mechanical communications ports may be configured to facilitate fluid being passed to and/or from the CSF management module 22 and/or facilitate electrical signals being passed to and/or from the inflammation management system 10. Example electrical communications ports may be or may include wired ports, wireless ports, radio frequency (RF) ports, Bluetooth ports, Near-Field Communication (NFC) ports, HDMI ports, Ethernet ports, VGA ports, serial ports, parallel ports, component video ports, S-video ports, composite audio/video ports, DVI ports, USB ports, optical ports, and/or other suitable ports. In some cases, electrical communications ports may include a mechanical connection feature.

The CSF management module 22 may include one or more hardware and/or software sub-modules 34. In one example, the CSF management module 22 may include a first sub-module 34*a*, a second sub-module 34*b*, and a N$^{th}$ sub-module 34N, where there are N sub-modules. The hardware and/or software sub-modules 34 may be swappable or exchangeable to fit different needs, as desired. For example, in one instance, a pump, a filtration treatment module and a waste control mechanism may be utilized for inflammation management; in another instance, a pump and a cooling treatment module may be utilized for inflammation management; and in a further instance, a pump, a filtration treatment module, and a cooling treatment module may be utilized. Other combinations of hardware and/or software sub-modules 34 may form or may be part of the CSF management module 22.

The circulation management module 23 may include one or more hardware and/or software modules (e.g., stored in memory for execution by the controller 16 and/or a processor of the circulation management module 23) and may be configured to control circulation of CSF through the inflammation management system 10 taking into account protocols of the CSF management module and other circulation requirements. In one example, the circulation management module 23 may be configured to maintain a predetermined CSF flow rate and/or a CSF pressure at or below a set point level and/or within a range of pressure levels. The circulation management module 23 may include a pump 36, but this is not required as the circulation management module 23 may rely on other pumps of the inflammation management system 10 to pump fluid through the inflammation management system 10 according to a circulation protocol taking into account needs of the CSF management module 22.

In operation, the controller 16 of the inflammation management system 10 may interact with a controller of the CSF management module 22 and/or individual controllers of the hardware and/or software sub-modules 34 to effect operation of one or more diagnoses and/or treatment protocols. In some cases, the controller 16 may be configured to interact with the hardware and/or software sub-modules 34 to facilitate control and/or operation of functionality that may be common to a plurality of protocols utilizing the hardware and/or software sub-modules 34. Common functionality that may be controlled and/or performed by the controller 16 may include, but is not limited to, real-time and trended pressure measurements and recordings, total volume circulated and time elapsed circulation measurements and recordings, circulation control (e.g., via pressure limiting to prevent pressure from exceeding a set point, maintaining a constant or predetermined flow to deliver circulation at a specified flow rate, etc.), alarm management, communications, system status updating, and/or other common functionality that may be required during operation of the one or more hardware and/or software sub-modules 34. In one example, the controller 16 may be configured to control and/or manage circulation (e.g., by sending control signals to a pump, a waste control mechanism, and/or other hardware and/or software sub-module 34) during diagnoses and/or treatment protocols utilizing the hardware and/or software sub-modules 34 (e.g., controlling and/or managing fluid circulation and/or pressure monitoring in a control loop).

The hardware and/or software sub-modules 34 may be configured to build off of the base or common functionality provided by the controller 16 and provide a specified function during a treatment protocol of a patient. A practitioner or institution may add and/or remove hardware and/or software sub-modules 34 from the CSF management module 22 to tailor the functionality of the CSF management module 22 to a particular diagnoses and/or treatment protocol, as desired. In one example, when the inflammation management system 10 is to be used to diagnose and/or treat a patient with a head injury, the treating institution and/or practitioner may install a cooling treatment module. In conjunction with appropriate peripheral components 12, the inflammation management system 10 may utilize the base or common functionality thereof (e.g., base or common functionality needed by hardware and/or software sub-modules 34, such as circulation management) and the functionality of the cooling treatment module to cool circulated fluid from a patient according to a cooling treatment protocol. In some cases, a cooling treatment protocol may be saved in software of the cooling treatment module, but this is not required and the cooling treatment protocol may be saved at another location and/or inputted to the inflammation management system 10 via the user interface 18.

In some cases, the CSF management module 22 may be housed in a housing of the inflammation management system 10. Alternatively or in addition, at least part of the CSF management module 22 may be separate from a housing of the inflammation management system 10. When the CSF management module 22 is housed in a housing of the inflammation management system 10, hardware portions of sub-modules may be swappable from the housing in a plug and play manner, but this is not required. In one example, if a cooling treatment module is needed in a first configuration, but a filtration treatment module is needed in a second configuration, the cooling treatment module may be removed from the housing of the inflammation management system 10 and replaced with the filtration treatment module. Further, when the inflammation management system, 10 includes all necessary hardware components, software sub-modules 34 may be swapped out and/or exchanged to implement desired protocols. Other swappable configurations are contemplated.

Figure 4:
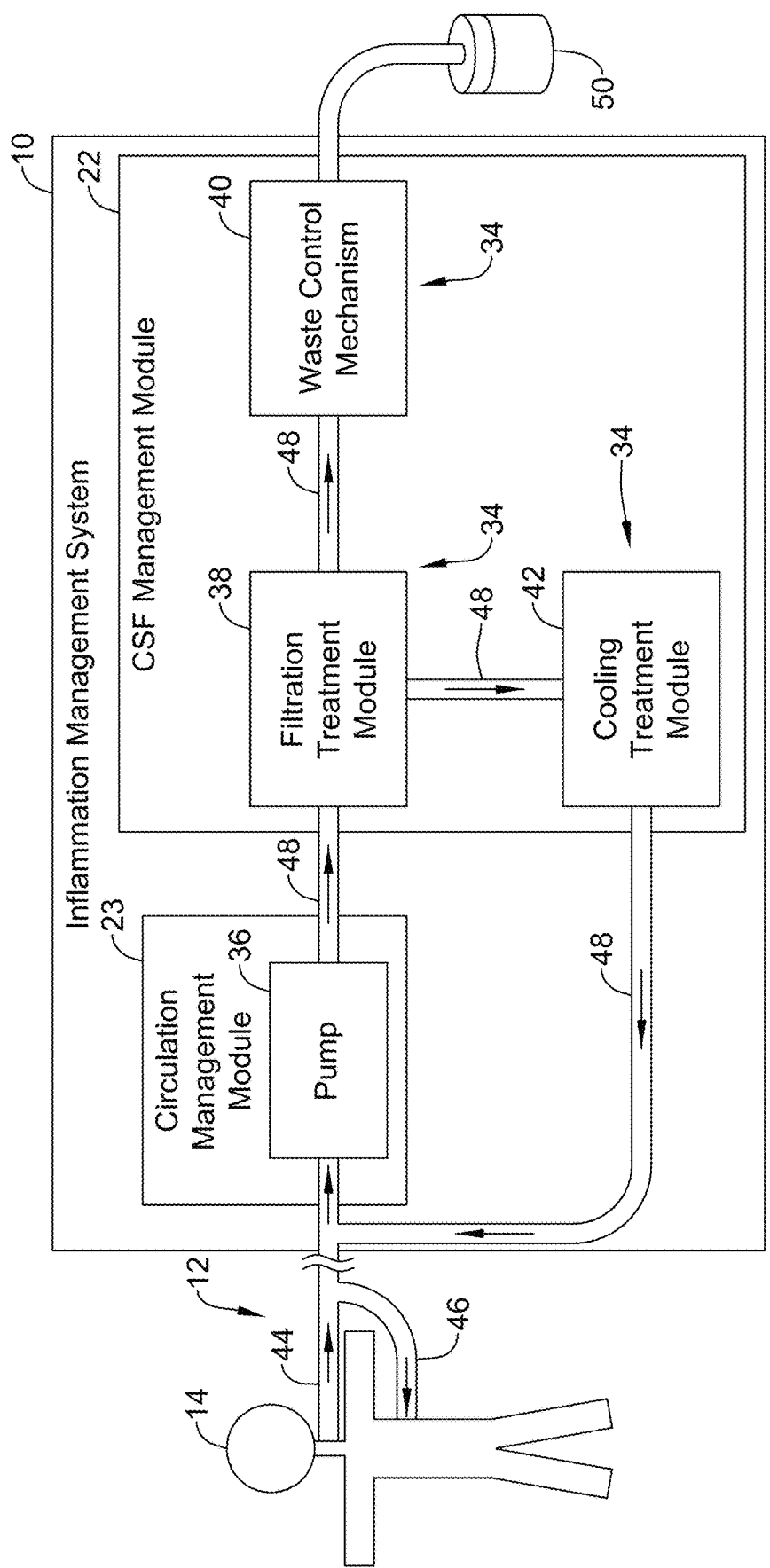
FIG. 4 is a schematic flow diagram of an inflammation management system in use with a patient.

FIG. 4 schematically depicts an illustrative configuration of the CSF management module 22 of the inflammation management system 10 in use with the patient 14 via a peripheral component 12 (e.g., a catheter). As discussed, the CSF management module 22 may include one or more hardware and/or software sub-modules 34. In the example CSF management module 22 depicted in FIG. 4, the hardware and/or software sub-modules 34 include a filtration treatment module 38, a waste control mechanism 40, and a cooling treatment module 42. As discussed above, the CSF management module 22 may include one or more additional or alternative hardware and/or software sub-modules 34 (e.g., up to the $N^{th}$ sub-module).

The pump 36, when included, of the circulation management module 23 may pump or assist in pumping fluid (e.g., CSF or other fluid) into, along, and/or through a fluid circuit of the inflammation management system 10. For example, the pump 36 may pump fluid into an inlet fluid pathway 44, through one or more hardware and/or software sub-modules 34, and out of an outlet fluid pathway 46. The CSF traveling through the inflammation management system 10 may travel along the fluid circuit through various pathways via a fluid line 48 having a lumen therein (e.g., tubing or other suitable mechanism forming a lumen and configured to facilitate maintaining a desired pressure within the fluid circuit by fluid tight connections at connection points, if any), where the lumen may be configured to facilitate travel of CSF along the fluid circuit from an inlet of the fluid line to the pump 36 and from the pump 36 to an outlet of the fluid line.

The pump 36 may be configured to pump CSF through the inflammation management system 10 with or without additional pumping mechanisms (e.g., pumps of the other hardware and/or software sub-modules 34 and/or other suitable pumps). Further, although the pump 36 and/or the circulation management module 23 are depicted and described herein as being separate from the CSF management module 22 as a permanent component of the inflammation management system 10, the pump 36 and/or the circulation management module 23 may be a hardware and/or software sub-module 34 of the CSF management module 22.

The pump 36 may be any suitable type of pump for pumping CSF through the inflammation management system 10. For example, the pump 36 may be a peristaltic pump or other suitable pump configured to apply a pressure to a fluid line to pump CSF from a patient, through the inflammation management system 10, and back to the patient. The pump 36 may be a single pump or multiple pumps configured to achieve a desired pressure and/or flow rate within the fluid line 48. Although the pump 36 is located upstream of the filtration treatment module 38, the waste control mechanism 40, and the cooling treatment module 42 in FIG. 4, the pump 36 may be located at any suitable location in the inflammation management system 10. In one example, the pump 36 may be located downstream of a fluid inlet of the inflammation management system 10 and upstream of a fluid outlet of the inflammation management system 10.

In some cases, the circulation management module 23 may utilize one or more sensors along a flow path of CSF through the inflammation management system 10 and/or peripheral components 12. The sensors, when included, may be configured to sense a measure within a lumen of the fluid line 48 extending from and/or forming the flow path. The circulation management module 23 may take into account, individually or in conjunction with the controller 16, measurements of a single sensor, two sensors, three sensors, or more sensors, as desired, at one or more locations along the flow path of the inflammation management system 10 when controlling circulation of CSF through the fluid line 48 with the pump 36.

The filtration treatment module 38 may include a hardware component and/or a software component. In one example, if the inflammation management system 10 includes a permanent filtering system, the filtration treatment module 38 of the CSF management module 22 may be a primarily software module that utilizes the functionality of the permanent components (e.g., hardware and software) of the inflammation management system 10 (e.g., the permanent filtering system, the controller 16, the user interface 18, the communications ports 20, the fluid line 48 and/or other flow paths, and/or other hardware components) to establish circulation rates (e.g., including, but not limited to, pulsatility) for the filtration treatment module 38 and/or the inflammation management system 10, monitor filtration time, control evacuation functionality, and/or perform one or more other suitable functions using the filtration treatment module 38. Such a software module may establish a predetermined filtering protocol, which may be modified by a user via the user interface 18 of the inflammation management system 10 or other user interface and/or may be exchanged for software modules establishing a different predetermined filtering protocol. The predetermined filtering protocol may be an example of a predetermined treatment or predetermined treatment protocol, among other example predetermined treatments or predetermined treatment protocols.

In some cases, the filtration treatment module 38 and/or a permanent filtering system of the inflammation management system 10 may include a hardware filter system to go along with the software module of the filtration treatment module 38. In some cases, a hardware filter system may include one or more pump components and/or one or more filters. Although other filtration treatment module configurations (e.g., other hardware and/or software components of the filtration treatment module) are contemplated, an example filtration treatment module is the pump/filtration system for pumping and/or filtering CSF that is described in U.S. Patent Application Ser. No. 62/693,225 filed on Jul. 2, 2018, and titled "SYSTEMS, CATHETERS, AND METHODS FOR TREATING ALONG THE CENTRAL NERVOUS SYSTEM", which is hereby incorporated by reference for all purposes.

In some cases, the hardware components of the filtration treatment module 38 may include one or more filters to filter contaminants (e.g., blood and/or other contaminants) from CSF. In one example, the filtration treatment module 38 may have a first filter and a second filter. In some instances, one or both of the first filter and the second filter may each be a tangential flow filter (TFF) or other suitable type of filter. For example, the first filter and/or the second filter may include a 5 kDa TFF, a 100 kDa TFF, a 0.2 µm TFF, a 0.45 µm TFF, or the like. Alternatively or in addition, the first filter and/or the second filter may include a dead-end filter (e.g., 5 kDa dead-end filter) and/or an electrofilter (e.g., a filter that excludes materials based on charge).

In at least some instances, the first filter and the second filter, when both are included, may be the same size and/or type (e.g., both the first filter and the second filter may be 100 kDa TFF). In other instances, the first filter and the second filter may differ in size and/or type (e.g., the first filter may be a 5 kDa filter and the second filter may be a 100 kDa TFF filter).

In some instances, the filtration treatment module 38 may include only one filter (e.g., the first filter). For example, the first filter may be a 5 kDa filter and the first filter may be the only filter. Alternatively, the filtration treatment module 38 may include more than two filters (e.g., the first filter, the second filter, and one or more additional filters).

The first filter may be configured to separate CSF, when CSF is the received fluid, into initial clean CSF (e.g., conditioned CSF) and initial waste CSF. The initial clean CSF from the first filter may flow to the cooling treatment module 42 and the initial waste CSF from the first filter may flow to the second filter.

The second filter, when included, may be configured to separate the received initial waste CSF into clean CSF (e.g., conditioned CSF) and waste CSF (e.g. final waste fluid). The clean CSF from the second filter may flow to the cooling treatment module 42 and the waste CSF may flow from the second filter to the waste control mechanism 40 (e.g., a manually operated or automated (e.g., via a controller) waste pump or other suitable waste control mechanism).

The waste control mechanism 40 (e.g., where the waste control mechanism 40 may be or may include a valve, a back pressure valve, a pinch valve, a flow metering mechanism, a pump, etc.) may receive waste fluid via the fluid line 48 from the filtration treatment module 38, as depicted in FIG. 4, and control a rate at which waste CSF is passed along a waste outlet pathway to a collection apparatus 50 for disposal (e.g., a rate at which the waste CSF is outputted from the filtration treatment module 38). The waste control mechanism 40 may be controlled manually and/or in an automated manner with a controller of the waste control mechanism 40 and/or with the controller 16 of the inflammation management system 10. Although other configurations of waste control mechanism 40 are contemplated, an example waste control mechanism is described in U.S. Patent Application Ser. No. 62/693,225, which was incorporated by reference for all purposes above.

The cooling treatment module 42 may be configured to chill fluid passing through the inflammation management system 10 and may include a hardware component and/or a software component. In some cases, the cooling treatment module 42 may be configured to receive fluid via the fluid line 48 from the filtration treatment module 38, but this is not required, and the cooling treatment module 42 may receive fluid via the fluid line 48 at one or more other locations along the fluid line 48.

The cooling treatment module 42 may include one or more pumps (e.g., in addition to or as an alternative to the pump 36) and/or one or more valves to facilitate controlling fluid circulation within the cooling treatment module 42 and/or otherwise within the inflammation management system 10, but this is not required and fluid circulation may be controlled by other pumps of the inflammation management system 10. The pumps and/or valve of the cooling treatment module 42, when included, may be configured to work with the pump 36 and or other pumps of the inflammation management system 10 to control fluid circulation through the fluid line 48.

A software component or module of the cooling treatment module 42 may establish a cooling protocol for the inflammation management system 10. The cooling protocol may be configured to set temperature set points for fluid passing through the inflammation management system 10 and/or the cooling treatment module 42, set rates at which a temperature of the fluid may be cooled (or, in some cases, warmed), set circulation rates (including, but not limited to, pulsatility) for fluid passing through the cooling treatment module 42 and/or the inflammation management system 10, establish hold times for fluids passing through the cooling treatment module 42 (e.g., a time it takes to reach a temperature set point based on ramp rates and circulation rates), and/or perform one or more other suitable functions using the cooling treatment module 42. The predetermined cooling protocol established by the software module of the cooling treatment module 42 may be modified by a user via the user interface 18 of the inflammation management system 10 or other user interface and/or may be exchanged for software modules establishing a different predetermined cooling protocol. The predetermined cooling protocol may be an example of a predetermined treatment or predetermined treatment protocol, among other example predetermined treatments or predetermined treatment protocols.

The cooling treatment module 42 may be configured to cool fluid passing there through in any suitable manner. In some cases, the cooling treatment module 42 may cool fluid passing there through via radiant cooling and/or other cooling techniques. For example, a surface of the fluid line 48 and/or other fluid pathway of the inflammation management system 10 may be cooled via coils, pre-cooled fluid, and/or cooled in one or more other manners and the cooled surface may remove heat from the fluid passing through the cooling treatment module 42 by radiation and/or convection. Alternatively or in addition, the cooling treatment module 42 may cool fluid passing there through by adding a pre-cooled fluid to the fluid passing through the cooling treatment module. In some cases, the added pre-cooled fluid may be a cooled saline, a cooled artificial CSF, and/or other suitable fluid. When adding pre-cooled fluid to the fluid passing through the cooling treatment module 42, an amount (e.g., volume or other amount) of fluid added to the fluid passing through the cooling treatment module 42 may be determined based on a function of a volume of material (e.g., fluid or other material) removed from the fluid during filtering of the fluid in order to maintain a desired balance or ratio fluid inputted to the inflammation management system 10 and fluid outputted from the inflammation management system 10. In one example, a volume of pre-cooled fluid added to the fluid passing through the cooling treatment module 42 may be equal to or substantially equal to a volume of fluid removed from the fluid passing through the filtration treatment module 38.

In the example depicted in FIG. 4, once fluid passing through the fluid line 48 of the inflammation management system 10 has passed through the filtration treatment module 38 and the cooling treatment module 42, the fluid may be outputted and returned to the patient. As depicted in FIG. 4, the fluid may be returned to the patient 14 at a location that is different than a location at which fluid was removed from the patient 14, but this is not required and the fluid that is returned to the patient 14 may be returned at the same location as or a location adjacent to the location at which the fluid was removed from the patient 14.

Figure 5:
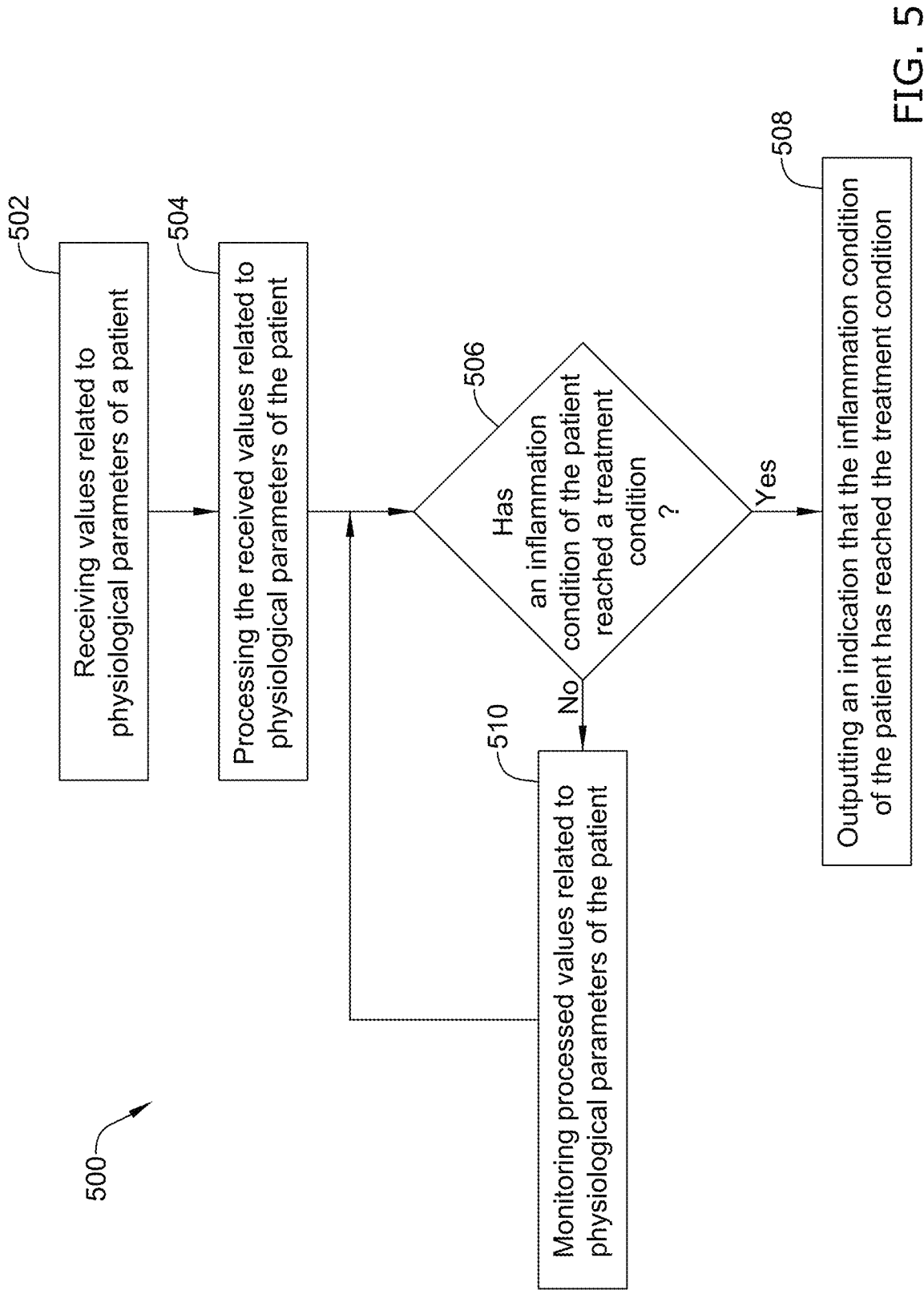
FIG. 5 is a schematic flow diagram of an example method of managing inflammation.

As discussed herein, the inflammation management system 10 may be used in methods of managing inflammation associated with a patient's brain. FIG. 5 depicts an illustrative method 500 of managing inflammation to diagnose and/or treat a patient's condition. Instructions for executing the method 500 may be stored in memory (e.g., the memory 26 or other suitable memory) for execution by a processor (e.g., the processor 24, a processor of a module or sub-module of the inflammation management system 10, and/or other suitable processor). In some cases, the method 500 may be performed entirely or at least partially with an inflammation management system (e.g., the inflammation management system 10 or other suitable inflammation management system).

As depicted in FIG. 5, the method 500 may include receiving 502 (e.g., obtaining) one or more values related to physiological parameters of a patient. The one or more values related to physiological parameters of the patient may be a measurement of a physiological parameter and/or one or more other suitable values determined based on the measurement of a physiological parameter of the patient. The one or more physiological parameters of the patient may be received and/or otherwise obtained from a component of the inflammation management system, a peripheral component of the inflammation management system, one or more sensors sensing a physiological parameter of the patient, an image capturing device (e.g., a camera, a CT scanning machine, a MM machine, X-ray machine, etc.), and/or other suitable data capturing devices configured to obtain data related to one or more physiological parameters of the patient. The one or more values related to physiological parameters of the patient may be stored or saved in the memory for access by a processor. The values received and/or stored or saved in the memory may relate to a single physiological parameter of the patient or two or more physiological parameters of the patient. In some cases, the one or more values related to physiological parameters of the patient may be received at the processor for processing from one or more input ports and/or from the memory.

Sensors in or otherwise connected to the inflammation management system may provide monitored measurements related to the physiological parameters of the patient. Example measurements of physiological parameters that may be monitored include, but are not limited to, measurements related to one or more of intracranial hemorrhage (ICH) volume, brain inflammation, white blood cell count (WBC), body temperature (TMP), heart rate variability (HRV), photoplethysmography (PPG), mass effect on a brain, midline shift (MLS) from a CT scan, blood volume (VOL), edema volume (PHE), intracranial pressure (ICP), water in the brain, brain tissue compliance (CMP), National Institute of Health Stroke Scale (NIHSS), level of consciousness (LOC), eye measurements with a pupilometer, motor skills (MTR), sensations (SNS), language skills (LNG), fluid management, blood pressure (BP), fluid input and output (I/O), cerebral perfusion pressure (CPP), sodium content (Na++), potassium content (K++), and/or measurements related to other suitable physiological parameters.

As values related to physiological parameters of the patient are obtained, those values and/or values related to the physiological parameters of the patient stored in the memory may be processed 504. The values related to physiological parameters of the patient may be processed using the processor of the inflammation management system and/or other suitable processor. In some cases, the values related to physiological parameters of the patient may be processed into one or more indexed values (e.g., the indexed values may be based on the values related to the physiological parameters of the patient and are discussed in greater detail below), which may be indicative of an inflammation condition or other suitable condition of the patient at a current time, indicative of how the inflammation condition has changed overtime, and/or indicative of how the inflammation condition is expected to change over a future time period. In some cases, the indexed value may be based, at least in part, on a value or values related to one (e.g., a single) physiological parameter. Alternatively, the indexed value may be based, at least in part, on values related to two or more physiological parameters.

The inflammation condition of the patient may be a condition of the patient that is related to a patient condition. The patient condition may be or may be related to a traumatic brain injury, a subarachnoid hemorrhage, intracranial hemorrhage, and/or other patient condition causing inflammation in, around, and/or affecting a brain of a patient and the inflammation condition may be a level of that inflammation. Typically an inflammation condition of a patient may be difficult to assess or define and use of the processed physiological parameters of the patient (e.g., use of indices as discussed herein) may help medical providers better understand the inflammation condition of a patient suffering from a condition causing inflammation in, around, and/or affecting the patient's brain.

As discussed above, the values related to the one or more physiological parameters of the patient may be processed into one or more indices. Each index may have an indexed value, where the indexed value may be based on measurements of the one or more physiological parameters of the patient. In some cases, the indexed value may be based on one or more sub-indices and each sub-index of the one or more sub-indices may be based on measurements of one or more physiological parameters of a patient.

In some cases, the values of one or more physiological parameters for an index based on values of physiological parameters of a patient may be weighted equally and in other cases, a value of the one or more physiological parameters for an index may be weighted differently than a value of one or more other physiological parameters taken into account for the index. Similarly, in some cases including an index of one or more sub-indices, each value of a sub-index used in an index may be weighted equally and in other cases, a value of one or more sub-indices for an index may be weighted differently than a value of one or more other sub-indices taken into account for the index.

An index value may be a value resulting from processing data in a particular manner for one or more parameters. The indexed value may be a value resulting from processing data obtained over time for a single parameter, a value resulting from processing data obtained over time for a plurality of parameters, a value resulting from processing data obtained at time, t, for a plurality of parameters, and/or other suitable value. Time, t, is a current time at which data is/was obtained.

Data for a single parameter may be obtained over time (e.g., from time, t, to a time, t, minus N units of time (time, t−N)) and an indexed value for the single parameter may be determined by applying an algorithm to the obtained data. In one example, an indexed value for data related to a single parameter may be a value of a rolling average of data obtained for the single parameter and/or a value resulting from applying one or more other suitable algorithms to the obtained data for the single parameter. In another example, an indexed value for data related to a plurality of parameters obtained at time, t, may be a value obtained by normalizing the data obtained at time, t, for each parameter of the plurality of parameters (e.g., normalizing data for each parameter on a scale from 1-100 or other suitable scale and/or normalizing in one or more other suitable manners) and taking an average of the normalized value for the parameters of the plurality of parameters and/or a value resulting from applying one or more other suitable algorithms to the obtained data at time, t, for the plurality of parameters. In another example, an indexed value for data related to a plurality of parameters obtained over time may be a value obtained by normalizing the data obtained over time for each parameter of the plurality of parameters (e.g., normalizing data for each parameter on a scale from 1-100 or other suitable scale and/or normalizing in one or more other suitable manners) and taking a rolling average of the normalized value for the parameters of the plurality of parameters and/or a value resulting from applying one or more other suitable algorithms to the data obtained over time for the plurality of parameters. Indices other than those resulting from averaging data are contemplated.

The indices based, at least in part, on values related to one or more physiological parameters a patient may be any suitable index type including, but not limited to, those discussed above. Example indices include, but are not limited to, an inflammation index, a mass effect index, a NUBS index, a fluid management index, Glasgow Coma Scale index, and/or other suitable indices based, at least in part, on values related to one or more physiological parameters of the patient.

The inflammation index may be indicative of brain inflammation (e.g., a brain inflammation index). The inflammation index may be based on, among other measurements, measurements of one or more of the following physiological parameters: white blood cell count (WBC), body temperature (TMP), heart rate variability (HRV), and photoplethysmography (PPG). In one example, an indexed value may be based, at least in part, on a value of the inflammation index when the inflammation index is based on a value for white blood cell count (WBC), a value for body temperature (TMP), a value for heart rate variability (HRV), and a value for photoplethysmography (PPG)

The mass effect index may be indicative of swelling of the brain. When the mass effect index is above a threshold level, an indication may be provided to take an action to address swelling of the brain. Alternatively or addition, when the mass effect index reaches the threshold level, an indication that a symptom related to swelling of the brain has a particular percentage chance of happening based on historical data and/or other suitable information. The mass effect index may be based on, among other measurements, measurements of one or more of the following physiological parameters: midline shift (MLS) from a CT scan, blood volume (VOL), edema volume (PHE), intracranial pressure (ICP), water in the brain, and brain tissue compliance (CMP). In one example, an indexed value may be based, at least in part, the mass effect index when the mass effect index is based on a value of the midline shift (MLS) from a CT scan, a value of the blood volume (VOL), a value of the edema volume (PHE), a value of the intracranial pressure (ICP), a value of an amount of water in the brain, and a value the brain tissue compliance (CMP).

The NIHSS index may be indicative of a severity of a stroke. The NIHSS index may be based on, among other measurements, measurements of one or more of the following physiological parameters: level of consciousness (LOC), eye measurements with a pupilometer, motor skills (MTR), sensations (SNS), and language skills (LNG). In one example, an indexed value may be based, at least in part, on the NIHSS index when the NIHSS index is based on a value of a level of consciousness (LOC), a value of eye measurements with a pupilometer, a value associated with motor skills (MTR), a value associated sensations (SNS), and a value associated with language skills (LNG).

The fluid management index may be indicative of fluid input into the body (e.g., fluid input from an IV drip and/or other suitable fluid input methods) and fluid output from the body (e.g., a fluid concentration of urine and/or other suitable fluid output methods). The fluid management index may be based on, among other measurements, measurements of one or more of the following physiological parameters: blood pressure (BP), fluid input and output (I/O), cerebral perfusion pressure (CPP), sodium content (Na++), and potassium content (K++). In one example, an indexed value may be based, at least in part, on the fluid management index when the fluid management index is based on a value of blood pressure (BP), a value associated with fluid input and output (I/O), a value of cerebral perfusion pressure (CPP), a value of sodium content (Na++), and a value of potassium content (K++).

The Glasgow Coma Scale index may be indicative of a conscious state of a patient. The Glasgow Coma Scale index may be based on, among other measurements, measurements of one or more of the following physiological parameters: eye measurements taken with a pupilometer, motor skills (MTR), and language skills (LNG). In one example, an indexed value may be based, at least in part, on the Glasgow Coma Scale index when the Glasgow Coma Scale index is based on a value of eye measurements taken with a pupilometer, a value associated with motor skills (MTR), and a value associated with language skills (LNG).

Other indices based on measurements of physiological parameters of a patient and/or other suitable factors are contemplated. Such other indices may be based on patient demographics, other suitable factors (e.g., other suitable physiological parameters, etc.), and/or other suitable combinations of factors.

In some cases, values of the inflammation index, the mass effect index, the NIHSS index, the fluid management index, the Glasgow Coma Scale index and/or other suitable indices, may be values of sub-indices that may be used or processed to determine a value of an index based on one or more sub-indices. A value of an index may be a function of one or more of a value of the inflammation index at a point in time or over time, a value of the mass effect index at a point of time or over time, a value of the NIHSS index at a point in time or over time, a value of the fluid management index at a point in time or over time, and/or a value of the Glasgow Coma Scale index at a point in time or over time.

An example index of sub-indices may be a NEUROWORSENING™ index. In some cases, the NEUROWORSENING™ index may indicate a patient condition deteriorating toward a threshold level prior to actually determining the patient condition has deteriorated to the threshold level (e.g., predicting a brain inflammation condition is deteriorating toward a threshold level before being able to diagnose the brain inflammation condition has reached the threshold level from an image of the patient's brain). In one example, the index may be based on one or more different sub-indices, where the one or more sub-indices may be selected or determined depending on a type of patient condition that is being monitored and may be indicative of the patient's inflammation condition. For example, when a patient is being monitored due to an intracranial hemorrhage patient condition, an example index of sub-indices may be based, at least in part, on the inflammation sub-index, the mass effect sub-index, and the NIHSS sub-index; when a patient is being monitored due to a subarachnoid hemorrhage patient condition, the index of sub-indices may be based, at least in part, on the inflammation sub-index, the mass effect sub-index, the fluid management sub-index, and the NIHSS sub-index; and when a patient is being monitored due to a traumatic brain injury patient condition, the index of sub-indices may be based, at least in part, on the inflammation sub-index, the mass effect sub-index, and the Glasgow Coma Scale index. Other combinations of sub-indices may be used to develop an index of sub-indices based, at least in part, on a patient condition for which an inflammation condition of a patient is being monitored. In some cases, the sub-indices and/or values related to the physiological parameters of the patient may be selected by individual medical providers to develop an index for a patient condition, as desired.

In some cases, the sub-indices and/or the index of sub-indices may be indicative of whether the inflammation condition is improving or worsening. In one example, if the values related to the physiological parameters of the patient are determined at a current time, the value of a sub-index may be representative of the patient's inflammation condition at the current time and when the values related to the physiological parameters of the patient are saved, the value of the sub-index at the current time may be based on previous values related to the physiological parameters of the patient and the current value related to the physiological parameters of the patient such that the value of the sub-index may be indicative of a trend in the patient's inflammation condition. Similarly, if the values of the sub-indices are determined at a current time, the value of the index of sub-indices may be representative of the patient's inflammation condition at the current time and when the values of the sub-indices are saved, the value of the index of the sub-indices at the current time may be based on previous values of the sub-indices and the current values of the sub-indices such that the value of the index of the sub-indices may be indicative of a trend over time of the patient's inflammation condition.

In some cases, the values of the plurality of physiological parameters of the patient, values of the sub-indices of the values of the plurality of physiological parameters of the patient, and/or the values of the index of the sub-indices may be depicted or otherwise displayed on a user interface (e.g., the user interface 18 and/or other suitable user interface). In one example, the values of the plurality of physiological parameters of the patient, values of the sub-indices of the values of the plurality of physiological parameters of the patient, and/or the values of the index of the sub-indices may be depicted on the user interface with graphs of the values versus time, directional indicators indicating whether the respective value is increasing, decreasing, or not changing from a previous time, ranges where the current value is shown relative to a possible range of values, and/or depicted in one or more other suitable manners. In some cases, a value of an index of sub-indices of values related to one or more physiological parameters of the patient may be displayed in a first pane of a display of a user interface relative to a range of possible values for the index of sub-indices (e.g., the NEUROWORSENING™ index depicted in the second pane 30b in FIG. 3) and values of the sub-indices of the values related to one or more physiological parameters of the patient may be displayed in the first plane (e.g., the second pane 30b in FIG. 3) or in a second pane of the display of the user interface relative to a predetermined time period. Displaying such values related to the one or more physiological parameters of the patient in close proximity to one another and/or in close proximity to other information (e.g., patient images, patient demographic information, etc.) facilitates providing a medical provider with a context for values of the one or more physiological parameters of the patient that the medical provider would typically not have as such information is typically provided to the medical provider, if at all, via multiple machines and/or printouts making it difficult to understand a context of any individual value or indexed value relative to the patient's condition or inflammation condition of the patient.

Based, at least in part, on the processed values related to one or more physiological parameters of the patient, the method 500 may include determining 506 whether an inflammation condition of the patient has reached a treatment condition. In one example, determining 506 whether an inflammation condition of the patient has reached the treatment condition may be based, at least in part, on the indexed value determined during the processing 504 of the values related to the one or more physiological parameters of the patient.

The treatment condition of the patient may be a level of the inflammation condition of the patient at which a treatment should occur and/or may be indicative of when a treatment should occur. Similar to the inflammation condition of the patient, the treatment condition of the patient may be difficult to assess or define and use of the processed physiological parameters of the patient (e.g., use of the indices discussed herein) and associated thresholds or ranges may facilitate determining when the inflammation condition of the patient has reached or will reach the treatment condition. In one example, the processed values related to the one or more physiological parameters of the patient may result in a value indicative of the patient's inflammation condition (e.g., an indexed value or other value indicative of the patient's inflammation condition) and when the value indicative of the patient's inflammation condition reaches a threshold value (e.g., a predetermined value, a trend level over time, a value based, at least in part, on one or more algorithms (e.g., a learning algorithm or other suitable algorithm) that use data from a plurality inflammation management systems or a global treatment protocol database, and/or other suitable threshold), it may be determined that the patient's inflammation condition has reached a treatment condition or will reach a treatment condition at a specifiable time in the future. In some cases, different determinations concerning an inflammation condition relative to a treatment condition may be made based on a value indicative of the patient's inflammation condition reaching different thresholds (e.g., different threshold levels) and/or based on a difference between the value and the threshold. When a value of a threshold is based, at least in part, on an algorithm that uses data from a plurality of inflammation management systems or a global treatment protocol database, the database may be a global database storing data from past implementations of treatment protocols from a plurality of remote inflammation management systems (e.g., such data may have information concerning, among other information, what treatment protocol was delivered for a patient condition, demographic information of the patient, when a treatment protocol was performed relative to an inflammation condition, what the values of any relevant indices were at the time of implementing or deciding to implement the treatment protocol, what the values of any relevant physiological parameters of the patient were at the time of implementing or deciding to implement the treatment protocol, etc.)

When it has been determined that the inflammation condition of the patient has reached a treatment condition based on the processed values related to physiological parameters of the patient, an indication that the inflammation condition of the patient has reached the treatment condition may be outputted 508. In some cases, the indication that the inflammation condition of the patient has reached the treatment condition may be outputted from the processor of the inflammation management system or other suitable processor via one or more ports in communication with the processor (e.g., the I/O ports 32, the communications ports 20, and/or other suitable port(s)). The outputting 508 of the indication may be performed automatically in response to identifying the inflammation condition of the patient has reached the treatment condition, but this is not required in all instances.

The indication that the inflammation condition of the patient has reached the treatment condition that is outputted 508 may be or may include any suitable indication. Example suitable indications include, but are not limited to, a control signal from the processor to a cerebrospinal fluid management module (e.g., a control signal to one or more submodules 34 of the cerebrospinal fluid management module 22 or other suitable components of a cerebrospinal fluid management module) to perform a treatment protocol on cerebrospinal fluid of the patient for addressing the patient's inflammation condition, a control signal to a user interface (e.g., the user interface 18, a display 30 of the user interface, and/or other suitable user interface) to display a suggested treatment protocol for treatment of the patient's inflammation condition, a control signal to the user interface to display a value on the display of the user interface (e.g., a value of an index on a pane, such as the first pane or other suitable pane, of the display), a control signal for turning on and/or off a light (e.g., a light of the user interface or other suitable light), a control signal for turning on and/or off a sound (e.g., from a speaker of the user interface or other suitable speaker), a control signal initiating an appointment invite or other suitable scheduling mechanism to schedule a medical provider to perform a treatment (e.g., a predetermined treatment and/or other suitable treatment) at a predetermined time in the future, and/or one or more other suitable indications.

The treatment protocol may be a set of instructions or list of treatments for treating the patient's inflammation condition. Example treatment protocols may include, but are not limited to, actuation of a CSF filtration treatment, actuation of a CSF cooling treatment, actuation of a CSF drainage treatment, actuation of one or more other suitable CSF therapies, surgery, etc.

When a treatment protocol is identified, suggested, or obtained, the processor may automatically select the treatment protocol based, at least in part, on processed values related to the physiological parameters, a threshold reached, and/or a difference between the processed values and a threshold. Such treatment protocols may be automatically identified or selected by the processor from a database of treatment protocols associated in a predetermined manner with the various patient conditions and values of the processed values related to physiological parameters of the patient. Alternatively or in addition, treatment protocols may be automatically identified or selected by the processor from the database of treatment protocols associated with the various patient conditions and values of the processed values related to physiological parameters based on one or more algorithms (e.g., a learning algorithm or other suitable algorithm). The database may be a global database storing data from past implementations of treatment protocols from a plurality of remote inflammation management systems (e.g., such data may have information concerning, among other information, what treatment protocol was delivered for a patient condition, demographic information of the patient, when a treatment protocol was performed relative to an inflammation condition, what values of any relevant indices were at the time of implementing or deciding to implement the treatment protocol, what values of any relevant physiological parameters of the patient were at the time of implementing or deciding to implement the treatment protocol, etc.) that is usable by the one or more algorithms to determine associations between treatment protocols and the various patient conditions and processed values of the values related to the physiological parameters of the patient that may be relevant to the patient's inflammation condition.

When it has been determined that the inflammation condition of the patient has not reached a treatment condition based on the processed values related to physiological parameters of the patient (e.g., a threshold or other suitable benchmark has not been reached), the processed values related to physiological parameters of the patient may be monitored 510 and the determining 506 of whether an inflammation condition of the patient has reached a treatment condition may be determined at a future time. In some cases, the steps 502-506 and 510 of the method 500 may be repeated and continuously performed at least until it has been determined the inflammation condition of the patient has reached the treatment condition. This, however, is not required. In some cases, the one or more steps of the method 500 may be repeated at predetermined time intervals and/or in response to manual actuation via the user interface or other suitable user interaction with the inflammation management system.

Figure 6:
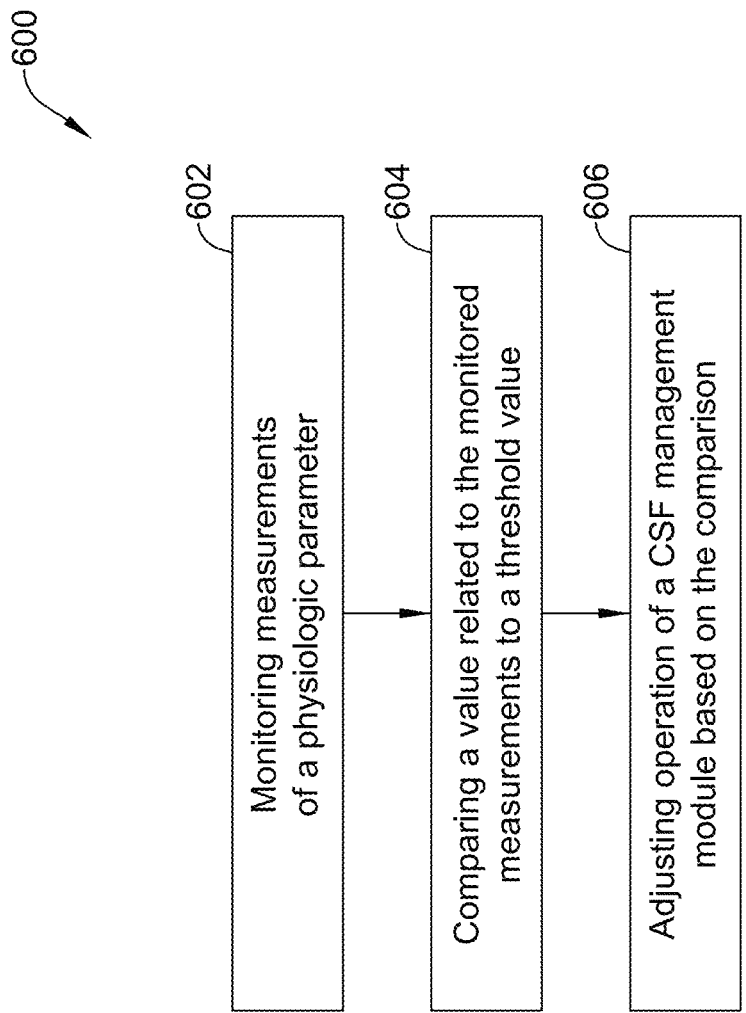
FIG. 6 is a schematic flow diagram of an example method of managing inflammation.

FIG. 6 depicts an illustrative method 600 of managing inflammation of a patient using an inflammation management system (e.g., the inflammation management system 10 and/or other suitable inflammation management systems). Instructions for executing the method 600 may be stored in memory (e.g., the memory 26 and/or other suitable memory) for execution by a processor (e.g., the processor 24, a processor of a module or sub-module of the inflammation management system 10, and/or other suitable processor).

Initially, although not required, a patient (e.g., the patient 14 or other suitable patient) may be connected to the inflammation management system via one or more peripheral components (e.g., the peripheral components 12 or other suitable peripheral components). Once the patient has been connected to the inflammation management system, the inflammation management system may monitor 602 measurements or values related to measurements of one or more physiological parameters of a patient over time on which CSF drainage, CSF cooling, CSF filtration, and/or other CSF therapies may be based. In operation, the monitoring 602 may be performed by a controller (e.g., the controller 16 or other suitable controller) of the inflammation management system.

The method 600 may include comparing 604 a value related to the monitored measurements of the one or more physiological parameters of the patient (e.g., an indexed value as discussed above with respect to FIG. 5 and/or other suitable value related to the one or more physiological parameters of the patient) to one or more threshold values (e.g., a threshold value determined in the manner discussed above with respect to FIG. 5 and/or determined in one or more other suitable manners). In one example, comparing 604 a value related to the monitored measurements of the one or more physiological parameters of the patient to one or more threshold values may include determining a difference between the value related to the monitored measurements of the one or more physiological parameters and the threshold value, but this is not required. In operation, the comparing 604 may be performed by the controller of the inflammation management system and/or other suitable controller.

Then, based on the comparison of the value related to the monitored measurements of the one or more physiological parameters to the threshold value, the method 600 may include adjusting 606 operation of a CSF management module (e.g., the CSF management module 22 and/or other suitable CSF management module). For example, if the value related to the monitored measurements of the one or more physiological parameters reaches or goes beyond a threshold value, operation of the CSF management module 22 may be adjusted (e.g., via a control signal) to initiate a filtration protocol using a filtration treatment module (e.g., the filtration treatment module 38 and/or other suitable filtration treatment module), a cooling protocol using a cooling treatment module (e.g., the cooling treatment module 42 and/or other suitable cooling treatment module), and/or other suitable treatment protocol (e.g., other suitable predetermined or learned/developed treatment protocols) using a sub-module (e.g., the hardware and/or software sub-modules 34 or other suitable sub-modules) of the CSF management module. In an additional or alternative example, when a difference between the value related to the monitored measurements of the one or more physiological parameters and the threshold value is determined, the operation of the CSF management module may be adjusted based on the determined difference between the value related to the monitored measurements of the one or more physiological parameters and the threshold value. Alternatively or in addition, operation of the CSF management module may be adjusted based on one or more additional or alternative factors.

Adjusting 606 the operation of the CSF management module may be automatically executed according to a treatment protocol (e.g., initiating: a treatment start protocol (e.g., which initiates other treatment protocols), a treatment stop protocol (e.g., which stops other treatment protocols), a filtration treatment protocol, a cooling treatment protocol, a suitable predetermined treatment protocol (e.g., which may or may not include the treatment start protocol, the treatment stop protocol, the filtration treatment protocol, the cooling treatment protocol and/or other suitable predetermined treatment protocols), and/or other suitable treatment protocols) of the CSF management module based on the comparison of the value related to the monitored measurements of the one or more physiological parameters to the threshold value. In some cases, a treatment start protocol may be started in response to determining the value related to the monitored measurements of the one or more physiological parameters reaches or goes beyond the threshold value a first time and a treatment stop protocol may be started in response to determining the value related to the monitored measurements of the one or more physiological parameters reaches or goes beyond the threshold value a second time after reaching or going beyond the threshold value the first time. Further, a type of treatment protocol (e.g., a type of predetermined treatment protocol, such as the cooling treatment protocol, the filtration treatment protocol, and/or other therapy or treatment protocols, and/or a type of non-predetermined treatment protocols (e.g., learned and/or developed treatment protocols)) may be automatically selected by the controller(s) of the inflammation management system based on a type or types of physiological parameters associated with the monitored measurements having a related value that reaches or goes beyond a threshold value and/or a value of a determined difference between the value related to the monitored measurements of the one or more physiological parameters and the threshold value and/or selected in the manner discussed above with respect to FIG. 5.

The automatic execution of the adjustments to the operation of the CSF management module may be effected using one or more controllers of the CSF management module and/or the controller(s) of the inflammation management system to treat and/or diagnose brain injuries. As an alternative to the automatic execution of the adjustments to the operation of the CSF management module, an alarm or other notification may be issued (e.g., via email, via a noise warning, a light warning, an indication on a user interface (e.g., the user interface 18 and/or other suitable user interface)), and a user may manually adjust operation of the CSF management module and/or manually initiate an adjustment of an operation of the CSF management module.

In addition to or as an alternative to adjusting an operation of the CSF management module (e.g., the circulation management module 23 and/or other suitable circulation management modules) in response to the value related to the monitored measurements of the one or more physiological parameters reaching or going beyond a threshold value, the controller 16 may adjust operation of the circulation management module to actively drain CSF from a patient. In some cases, the operation of the circulation management module to actively drain CSF form the patient may occur while adjusting operation of the cooling treatment module to cool CSF for a predetermined amount of time, adjusting operation of the filtration treatment module to filter CSF at a predetermined flow rate, and/or adjusting operation of the CSF management module in one or more other manners.

The inflammation management system 10 may be used to treat a number of conditions. Some of the contemplated conditions include cancer. For example, Leptomeningeal Metastases (LM) is a condition in which cells from a primary solid or hematological tumor metastasize, invade the subarachnoid space (SAS), and spread throughout the cerebrospinal fluid (CSF), resulting in seeding of the leptomeninges along the surface of the central nervous system (CNS). LM represents a late event of cancer progression and the most frequent symptoms include multiple cranial nerve deficits, motor deficits, altered mental status, headache, and radicular pain. The incidence of LM is estimated at 3-5% of cancer patients and has been increasing, due to longer overall survival in cancer patients. LM presents a difficult challenge in metastatic cancer treatment plans, resulting in a devastating prognosis and median survival of 4 months because of lack of effective access and therapies. Systemic therapy with anti-cancer drugs including methotrexate (MTX), cytarabine and thiotepa are not as effective due to poor penetration of the blood-brain barrier (BBB). Intrathecal (IT) drug delivery systems, including Ommaya reservoirs, have been associated with longer overall survival; however, they require repeated injections and rely on passive diffusion. Future therapies that target the entire CNS and enhance the distribution of IT drugs could further improve survival. CSF is produced at approximately 20 ml/hr, with a total volume of ~150 ml, resulting in a turnover, on average, of three times per day. The production rate of CSF is independent of intracranial pressure (ICP). As LM can block the outflow paths of CSF, patients are at serious risk of hydrocephalus and elevated ICP. Additionally, the relative isolation of the CSF by the BBB and blood-CSF barriers, presents a unique environment for tumor survival.

The inflammation management system 10 may have the ability to rapidly clear a number of CSF pathogens and cells, as well as to enhance drug delivery in the CSF. For example, the inflammation management system 10 may be used to improve the LM outcome by 1) enhanced exposure and circulation of specific anticancer agents (MTX delivered through an Ommaya reservoir, a catheter, or both) throughout the SAS, (2) local filtering of CSF to remove cancer-spreading circulating tumor cells (CTCs), (3) control of ICP via CSF drainage, (4) filtration of tumor cells (e.g., living and/or dead tumor cells that may clog the natural reabsorption of the CSF via the arachnoid granulations and lymphatic system The inflammation management system 10 may also be used to reduce the concentration of a drug (e.g., a chemotherapy agent such as methotrexate) in the CSF (e.g., in order to remove excess drug, reduce toxicity, etc.).

As alluded to herein, treatment methods are contemplated that include infusing a chemotherapy agent into the patient. In some instances, the chemotherapy agent is methotrexate. Other chemotherapy agents are contemplated. The chemotherapy agent may be infused into the CNS via an Ommaya reservoir (and/or or a similar device including, for example, a Rickham device) implanted in the ventricles of the patient, as is standard of care in these patients. In addition or in the alternative, the chemotherapy agent may be infused into the patient using a catheter. For example, the chemotherapy agent may be added to a clean CSF outlet pathway, to one of the ports of the catheter, via a separate device disposed adjacent to the catheter, or in another suitable manner. The circulation of CSF by the inflammation management system 10 may help to circulate the chemotherapy agent throughout the cerebrospinal space and/or the CNS.

Another contemplated condition that the inflammation management system 10 may be used to treat is Amyotrophic Lateral Sclerosis (ALS). For example, the pathology of ALS may be correlated with overstimulation of glutamatergic functions/pathways with a corresponding excitotoxicity, increased calcium levels, and/or the generation of reactive oxygen species. Oxidative stress may be involved in pathological mechanisms of ALS via cell death-related release of pro-oxidative compounds and redox-active iron, mitochondrial dysfunction, inflammation, and excitotoxicity. The inflammation management system 10 may be used to help reduce/clear the CSF of oxidative and/or inflammatory agents (e.g., including free radicals, cytokines, chemokines, white blood cells) such as those correlated with the pathology of ALS. Some examples of materials that may be reduced/removed as part of treating ALS may include one or more of insoluble superoxide dismutase-1 (SOD1), glutamate, neurofilament protein, and anti-GM1 ganglioside antibodies.

In some instances, the oxidative and/or inflammatory agents may carry an electrical charge. Removal of such materials may be enhanced utilizing electrofiltration (e.g., a filter having an electrical charge). Accordingly, in at least some instances, the first filter, the second filter, both, and/or one or more other filter may include an electrically charged filter (electrofilter). In some of these and in other instances, the first filter, the second filter, or both may include an immunoaffinity column, a size exclusion column, an anionic exchange column, a cationic exchange column, and a Protein A or Protein G column.

In addition to removing CSF-borne pathological mediators correlated with ALS, the inflammation management system 10 may also be used to deliver one or more drugs to the CSF. Such treatments may help further reduce oxidative and/or inflammatory agents. In some instances, the drug may be added to the clean CSF outlet pathway (e.g., the return outlet), to one of the ports of the catheter, via a separate device disposed agent to the catheter, or in another suitable manner. The circulation of CSF by the inflammation management system 10 may help to circulate the drug throughout the cerebrospinal space and/or the CNS. Some example drugs that may be utilized may include riluzole, edaravone, or the like.

Another contemplated condition that the inflammation management system 10 may be used to treat is herpes simplex encephalitis (HSE). HSE is known to cause severe neuroinflammation, cerebral edema and hemorrhagic necrosis with resultant increases in intracranial pressure (ICP). While medical management has been standardized, aggressive combined medical and surgical management including decompressive craniectomy and/or temporal lobectomy is often performed due to uncontrolled ICP, neuroinflammation and cerebral edema. The production of reactive oxygen species (ROS) are also believed to be a component of natural defenses to viral infection. However, the lipid-rich environment of the CNS may be susceptible to oxidative damage. Thus, oxidative damage can be correlated with HSE infection.

The inflammation management system 10 may be used to remove oxidative and/or inflammatory agents (e.g., including free radicals, cytokines, chemokines, white blood cells)

such as those correlated with the pathology of HSE. In some instances, the oxidative and/or inflammatory agents may carry an electrical charge. Removal of such materials may be enhanced utilizing electrofiltration (e.g., a filter having an electrical charge). Accordingly, in at least some instances, the first filter, the second filter, or both may include an electrically charged filter (electrofilter).

Another contemplated condition that the inflammation management system 10 may be used to treat is human immunodeficiency virus (HIV) and/or acquired immune deficiency system (AIDS). HIV infection of the CNS can lead to a number of complications including meningitis, acute inflammatory polyneuropathy (AIDP), immune reconstitution inflammatory syndrome (IRIS)—initiated by introduction of antiretroviral therapy, chronic inflammatory polyneuropathy (CIDP), distal symmetric polyneuropathy (DSP), progressive multifocal leuko-encephalopathy (PML), and HIV-associated neurocognitive disorders (HAND). The inflammation management system 10 may be designed to filter/reduce/remove a number of different strains of HIV from the CNS. This can reduce viral load in the CSF and/or reduce complications associated with HIV infection in the CNS. In addition, the inflammation management system 10 may be designed to filter/reduce/remove a number of different inflammatory agents associated with HIV from the CNS.

Another contemplated condition that the inflammation management system 10 may be used to treat is multiple sclerosis (MS). Two subtypes, Clinically Isolated Syndrome (CIS) and Relapsing-Remitting Multiple Sclerosis (RRMS), represent the disease absent progression, while Primary Progressive (PPMS) and Secondary Progressive (SPMS) represent patients with progressive disease from the start or after RRMS, respectively. Neuroinflammation leading to multifocal lesion formation, demyelination, axonal damage and consequent neurodegeneration are hallmarks of the disease. Current treatments may be classified as including (1) anti-inflammatory naturally-occurring molecules (IFN-beta), (2) molecules that stimulate anti-inflammatory (glatiramer acetate) or inhibit autoreactive (teriflunomide) cell proliferation, (3) immunosuppressive monoclonal antibodies (natalizumab), (4) molecules that bind transcription factors to enhance anti-inflammatory mechanisms or suppress pro-inflammatory ones (dimethyl fumarate), and (5) agents that inhibit egress of lymphocytes from lymphoid tissue to the CNS (fingolomod). In some instances, the inflammation management system 10 may be designed to filter/reduce/remove a number of different inflammatory agents associated with MS including immune cells (immunoglobins, neutrophils, lymphocytes, monocytes, and the like), oxidative and/or inflammatory agents (e.g., including free radicals, cytokines, chemokines, white blood cells) such as those correlated with the pathology of MS, and the like. This can help treat MS and/or improve the symptoms thereof.

Another contemplated condition that the inflammation management system 10 may be used to treat is Guillain-Barré syndrome (GBS). GBS is the most common cause of acute paralytic neuropathy worldwide. Acute motor axonal neuropathy (AMAN) and acute inflammatory demyelinating polyneuropathy (AIDP) are the main phenotypes. GBS may arise in individuals through a combination of host genetic and environmental factors, and preceding infection by pathogens including Campylobacter jejuni and Zika virus. Prevailing mechanisms of action implicate molecular mimicry of foreign antigen and gangliosidic residues resulting in the development of autoantibodies which recognize myelin or axonal components and initiate an inflammatory immune response including macrophage and/or lymphocytic infiltration, complement deposition, and cytokine production. CSF analysis shows elevated protein (>400 mg/L) and the absence of pleocytosis in 90% of patients. Elevated levels of neuroinflammatory cytokines and other proteins involved in the pathology have been noted, though specific immunological protein profiles of GBS CSF are heterogenous. In some of these and in other instances, a second catheter may be used to infuse a drug into the cranial region.

Current treatments for GB S may include plasma exchange (PE) or intravenous immunoglobulins (IVIg) with supportive care. Based on protein abnormalities of the CSF in GBS patients, including elevated levels of inflammatory cytokines TNF-α and IL-6[7], anti-ganglioside antibodies, and activated complement components, filtration of CSF to reduce/remove inflammatory may help to reduce GBS systems and/or treat GBS. In some instances, The inflammation management system 10 may be designed to filter/reduce/remove a number of different inflammatory agents associated with GBS including immune cells (immunoglobins, neutrophils, lymphocytes, monocytes, and the like), oxidative and/or inflammatory agents (e.g., including free radicals, cytokines, chemokines, white blood cells) such as those correlated with the pathology of GBS, and the like. This can help treat GBS and/or improve the symptoms thereof. In some instances, the inflammation management system 10 may include a 5 kDa filter when used for treating GBS. Other filter sizes are contemplated including those disclosed herein. For example, the inflammation management system 10 may include a 5 kDa tangential flow filter, a 100 kDa tangential flow filter, an electrofilter, or a combination thereof.

Another contemplated condition that the inflammation management system 10 may be used to treat is meningitis. Bacterial meningitis occurs when pathogenic bacteria enter the subarachnoid space and cause a pyogenic inflammatory response. Gram-negative bacterial meningitis (GBM) is a devastating condition that occurs when gram-negative bacteria invade the central nervous system (CNS). There are 30,000 US cases and over 1 million cases of GBM worldwide annually. When bacterial infections are manifested as GBM, it creates an extreme burden of mortality, often exceeding 30%, and morbidity to the patient and is very difficult for clinicians to treat, even when caused by bacteria susceptible to standard antibiotics. It is seen most commonly in children or immunocompromised patients, such as those with HIV, post organ-transplant or post-neurosurgical procedures. Current treatment guidelines include intravenous cephalosporins or carbapenems or polymycin for at least 10 days to 2 weeks. In the presence of gram-negative enteric bacterial meningitis, classically occurring around trauma and neurosurgical procedures, highly resistant bacteria can cause disease. Antibiotics like aminoglycosides and polymycins are considered for treatment but the therapeutic-toxic ratio is poor for these agents with systemic use in CNS disease and there may be no optimal treatments.

Three key gram-negative pathogens that have been deemed critical priority include Pseudomonas, Acinetobacter and Klebsiella (PAK). These gram-negative bacteria can cause severe and often deadly infections such as pneumonia, bloodstream infections and, specifically, nosocomial meningitis. These bacteria have become resistant to a large number of antibiotics, including carbapenems and third generation cephalosporins—the best available antibiotics for treating multidrug-resistant bacterial meningitis. The world health organization acknowledges that multi-modal approaches are needed and that waiting any longer will cause further public health problems and dramatically impact patient care and survival. This raises the very real possibility of GBM infections that are untreatable by presently available antibiotics. This return to the pre-antibiotic era has unfortunately become a reality in many parts of the world.

Reduction in CSF organism burden is the single most important factor impacting survival and is linked to a better overall clinical outcome. The rapid reduction in CSF organism burden is important, with sterilization of the CSF in the first 24 hours. Optimization of the antibiotic effect depends directly on the organism load that is present and on the direct activity of antibiotic therapy being started early in infection. Determining which antibiotic agent will be most effective is becoming increasingly more difficult in the face of drug-resistant bacteria such as PAK. Clinical data for new antibiotics for bacterial meningitis simply have not kept pace with the rise of resistance, and the development of new therapeutic approaches is urgently needed. Additionally, experimental animal models have shown that outcome from bacterial meningitis are related to the severity of inflammation in the subarachnoid space (SAS) and could potentially be improved by modulation of the inflammatory response.

The inflammation management system 10 may provide an innovative new treatment option that provides direct access to the CSF and creates active circulation combined with targeted pathogen removal. This may provide a novel therapeutic approach that rapidly reduces CFUs and CSF bacterial burden and translates to reduced morbidity and mortality from bacterial meningitis.

Accordingly, the present methods provide for ameliorating or reducing the symptoms of bacterial meningitis by reducing or eliminating the presence of one or more of bacterial pathogens and/or their associated endotoxins and/or cytokines in the CSF using the inflammation management system 10. The methods comprise removing CSF from a patient, removing at least one of the bacterial pathogens, and/or endotoxins associated with the bacterial pathogens, and/or cytokines from the CSF, and returning the endogenous CSF to the patient, wherein the removing and returning steps are performed concurrently during at least a portion of the treatment. In some embodiments, the cytokines are selected from the group consisting of IL-1ra, IL-6, TNF, CRP, and CXCL10, or combinations thereof.

In some of these and in other instances, the methods provide for ameliorating or reducing the symptoms of bacterial meningitis by introducing a catheter through a spinal access site into a spinal CSF space of a patient, advancing the catheter through the spinal CSF space toward the brain so that openings of the catheter are disposed within the CSF space and spaced-apart by a preselected distance or adjusted to an appropriate distance, withdrawing CSF through at least some of the openings in the catheter, removing at least one of bacterial pathogens and/or their associated endotoxins and/or cytokines from the withdrawn CSF with the inflammation management system 10 (thereby conditioning the CSF), and returning the conditioned CSF through the other of the openings in the catheter.

Fungal meningitis (FM) is an infection of the meninges of the central nervous system that manifests from the dissemination of any major fungal pathogen into the subarachnoid space (SAS) via the cerebrospinal fluid (CSF). Cryptococcal Meningitis (CM) is caused by *Cryptococcus neoformans* and is the most common cause of fungal meningitis in adults. Other agents causative of fungal meningitis include: *C. Gattii, Blastomyces, Histoplasma, Coccidioides*. Treatment for CM is based on an induction, consolidation, and maintenance approach with antifungals and is well defined elsewhere, but is associated with continued high morbidity and mortality. Drug discovery programs are limited by poor penetration of the Blood Brain Barrier (BBB). Because of this, we developed an alternative catheter-based extracorporeal filtration system (Neurapheresis Therapy) for the filtration of infected CSF. Here we describe the in vitro characterization of Neurapheresis Therapy as an alternative mechanical intervention for filtration of *C. neoformans* cells, polysaccharide antigen, and inflammatory mediators from infected CSF.

The inflammation management system 10 may provide an innovative new treatment option that provides direct access to the CSF and creates active circulation combined with targeted pathogen removal. This may provide a novel therapeutic approach that rapidly reduces CFUs and CSF fungal burden and translates to reduced morbidity and mortality from fungal meningitis. In at least some instances, the inflammation management system 10 may include one or more filters designed to exclude the passage of fungi therethrough such as *C. neoformans*. In some of these and in other instances, the inflammation management system 10 may include one or more filters designed to exclude fungi (e.g., *C. neoformans*), associated antigens, and/or inflammatory agents. In at least some instances, a single pass of CSF through a 5 kDa TFF and/or a 100 kDa TFF may be sufficient to exclude *C. neoformans* or other reduce the CFUs of *C. neoformans* in the CSF. In addition, a 5 kDa TFF and/or a 100 kDa TFF may be sufficient to exclude or otherwise reduce *C. neoformans* antigen from the CSF. Furthermore, a 5 kDa and/or 100 kDa TFF may also exclude a number of neuroinflammatory agents such as IL-1ra, IL-6, TNF, CRP, and/or CXCL 10/IP-10 from the CSF.

Accordingly, the present methods provide for ameliorating or reducing the symptoms of fungal meningitis by reducing or eliminating the presence of one or more of fungal pathogens and/or their associated antigens (e.g., Cryptococcal antigen) and/or cytokines in the CSF using the inflammation management system 10. The methods comprise removing CSF from a patient, as described herein; removing at least one of the fungal pathogens, and/or antigens associated with the fungal pathogens, and/or cytokines from the CSF, and returning the endogenous CSF to the patient, wherein the removing and returning steps are performed concurrently during at least a portion of the treatment. In some embodiments, the cytokines are selected from the group consisting of IL-1ra, IL-6, TNF, CRP, and CXCL10, or combinations thereof. The fungus/fungi and/or antigens and/or cytokines can be removed from the CSF using one or more filtration system. A 5 kDa and/or 100 kDa TFF may also exclude a number of neuroinflammatory agents such as IL-1ra, IL-6, TNF, CRP, and/or CXCL 10/IP-10.

In some of these and in other instances, the methods provide for ameliorating or reducing the symptoms of fungal meningitis by introducing the catheter through a spinal access site into a spinal CSF space of a patient, advancing the catheter through the spinal CSF space toward the brain so that the openings of the catheter are disposed within the CSF space and spaced-apart by a preselected distance or adjusted to an appropriate distance, withdrawing CSF through at least some of the openings in the catheter, removing at least one of fungal pathogens and/or their associated antigens and/or cytokines from the withdrawn CSF with the inflammation management system 10 (thereby conditioning the CSF), and returning the conditioned CSF through the other of the openings in the catheter.

In at least some instances, the inflammation management system 10 may be used to deliver drugs to portions of the CNS. For example, some treatments for CM may include the administration of intravenous and oral antifungals such as amphotericin B (AmB) and flucytosine. Generally, intrathecal (IT) AmB boluses may be associated with neurotoxic drug concentrations near the injection site. The use of the inflammation management system 10 may allow for the IT infusion of AmB and/or other drugs. Unexpectedly, the inflammation management system 10 may also be used to reduce, filter, or otherwise remove some drugs such as AmB. Because of this, the dosage of AmB can be precisely titrated to a desired dose. If levels of AmB reach undesired levels (e.g., undesired high levels), the inflammation management system 10 can be used to quickly remove unwanted quantities of AmB from the CSF.

The inflammation management system 10 can also be used to deliver a number of other drugs including drugs where the difference between therapeutic doses and toxic doses are relatively small. For example, a drug may be infused into the CSF using the inflammation management system 10. If signs of toxicity are observed or if measurements of the drug concentration in the CSF is higher than desired, the inflammation management system 10 can be used to rapidly remove the drug from the CSF. Thus, the inflammation management system 10 can be used for controlled delivery of drugs into the CSF of patients and the rapid removal of drugs from the CSF, as desired.

The inflammation management system 10 may also help to reduce ICP associated with a number of conditions. For example, some conditions (e.g., such as cancer, HSE, and others) may be associated with higher ICP due to cells (e.g., tumor cells, etc.), inflammatory agents, and the like blocking, clogging, or otherwise impacting natural pathways for reabsorption of CSF. By using the inflammation management system 10, materials that might blocking natural reabsorption pathways can be removed/reduced, thereby desirably impacting the volume of CSF and reducing ICP.

Systems are also contemplated that utilize a first port for providing access to the cerebrospinal space and/or the CNS at a first location and a second port for providing access the cerebrospinal space and/or the CNS at a second location. Such ports may be implanted acutely or for extended periods of time. In some instances, the ports may allow for infusion of substances to the cerebrospinal space and/or the CNS, removal of substances from the cerebrospinal space and/or the CNS, or both. One or both of the ports may be or otherwise be similar to an Ommaya reservoir. The ports may be designed to be used with a tube/catheter, the inflammation management system 10. For example, a first tube and/or first catheter may be connected with or otherwise be connectable to one of the ports and a second tube and/or second catheter may be connected with or otherwise be connectable to the other port. CSF may be removed from the patient (e.g., using a tube, either the first or the second catheter, or the like) and filtered by the inflammation management system 10. In some instances, the filtered CSF may be returned to the patient using the same tube/catheter. In other instances, the filtered CSF may be returned to the patient using the other tube/catheter. In other words, CSF may be removed from the patient using a catheter at the first port, filtered, and then returned to the patient using a catheter at the second port. This may form a loop-like pathway the helps to circulate CSF through the cerebrospinal space and/or the CNS. The ports may be positioned along the patient in a manner that helps to facilitate circulation of CSF. For example, one of the ports may be positioned at the cranium of the patient (e.g., which may include providing access to the ventricles of the brain) and the other may be positioned along a lumbar region of the spine (e.g., which may provide access to the cerebrospinal space at a position adjacent to the lumbar space). Other locations are contemplated.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It should be noted that delivery sheath and delivery catheter may be used interchangeably for purposes of this description. The exemplary drawings are for purposes of illustration only and the dimensions, positions, order and relative sizes reflected in the drawings attached hereto may vary.

U.S. Patent Application Pub. No. US 2016/0051801 is incorporated herein by reference. U.S. Pat. No. 8,435,204 is incorporated herein by reference. U.S. Patent Application No. 62/568,412 is incorporated herein by reference. U.S. Patent Application No. 62/598,846 is incorporated herein by reference.

The above specification, examples and data provide a complete description of the structure and use of exemplary embodiments of the disclosure as claimed below. Although various embodiments of the disclosure as claimed have been described above with a certain degree of particularity, or with reference to one or more individual embodiments, those skilled in the art could make numerous alterations to the disclosed embodiments without departing from the spirit or scope of this disclosure. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the disclosure.

What is claimed is:

1. An inflammation management system, the system comprising:
    a controller;
    a user interface in communication with the controller;
    a cerebrospinal fluid management system in communication with the controller;
    wherein the controller is configured to:
        monitor measurements of one or more physiological parameters of a patient;
        compare a value related to the monitored measurements of the one or more physiological parameters to a threshold value; and
        control the cerebrospinal fluid management system based on the comparison of the value related to the monitored measurements of the one or more physiological parameters to the threshold value, and
    wherein the user interface is configured to display a medical image of the patient in a selectable pane and one or both of the measurements of the one or more physiological parameters of a patient and the value related to the monitored measurements of the one or more physiological parameters in a real-time updating pane positioned on the user interface simultaneously with and adjacent to the selectable pane, and wherein the selectable pane is configured to be selected and the user interface is configured to change what is displayed on the selectable pane in response to the selectable pane being selected.

2. The system of claim 1, wherein the controller is configured to automatically control the cerebrospinal fluid management system to perform a treatment on cerebrospinal fluid of the patient when the value related to the monitored measurements of the one or more physiological parameters reaches or goes beyond the threshold value.

3. The system of claim 2, wherein the treatment on cerebrospinal fluid of the patient is a predetermined treatment based on one or both of:
 a type of physiological parameter associated with the monitored measurements; and
 the comparison of the value related to the monitored measurements of the one or more physiological parameters.

4. The system of claim 1, wherein the value related to the monitored measurements of the one or more physiological parameters is an indexed value related to measurements of two or more physiological parameters of the patient.

5. The system of claim 4, wherein the indexed value is a value of an index based on measurements of the two or more physiological parameters of the patient.

6. The system of claim 1, wherein the one or more physiological parameters include one or more physiological parameters selected from a group consisting of intracranial pressure, cerebral pressure perfusion, mean arterial pressure, heart rate, brain oxygenation, cerebral blood flow, and a cytokine level.

7. The system of claim 1, wherein the cerebrospinal fluid management system comprises one or both of:
 a cooling treatment module; and
 a filtration treatment module.

8. The system of claim 1, wherein the cerebrospinal fluid management system comprises a pump configured to pump cerebrospinal fluid from the patient to a treatment system.

9. The system of claim 3, wherein the user interface is configured to receive inputs that modify the predetermined treatment.

10. A method of managing inflammation, the method comprising:
 monitoring measurements of one or more physiological parameters of a patient over time;
 comparing a value related to the monitored measurements of the one or more physiological parameters to a threshold value;
 displaying a medical image of the patient in a selectable pane on a user interface, wherein the selectable pane is configured to be selected and what is displayed on the selectable pane is changed in response to the selectable pane being selected;
 displaying one or both of the measurements of the one or more physiological parameters of a patient and the value related to the monitored measurements of the one or more physiological parameters in a real-time updating pane on the user interface simultaneously with and adjacent to the selectable pane;
 selecting a predetermined treatment protocol from a database of predetermined treatment protocols; and
 adjusting operation of a cerebrospinal fluid management system according to the selected predetermined treatment based on the comparison of the value related to the monitored measurements of the one or more physiological parameters to the threshold value.

11. The method of claim 10, further comprising:
 determining a difference between the value related to the monitored measurements of the one or more physiological parameters and the threshold value; and
 wherein the selecting the predetermined treatment protocol from the database of predetermine treatment protocols is based on the determined difference between the value related to the monitored measurements of the one or more physiological parameters and the threshold value.

12. The method of claim 10, wherein the predetermined treatment protocol is a treatment start protocol selected in response to the value related to the monitored measurements of the one or more physiological parameters reaching or going beyond the threshold value a first time.

13. The method of claim 10, wherein the predetermined treatment protocol is a treatment stop protocol selected in response to the value related to the monitored measurements of the one or more physiological parameters reaching or going beyond the threshold value.

14. The method of claim 10, wherein the predetermined treatment protocol is selected from the database of predetermined treatment protocols based on one or both of:
 a type of physiological parameter associated with the monitored measurements; and
 the comparison of the value related to the monitored measurements of the one or more physiological parameters to the threshold value.

15. The method of claim 10, wherein the adjusting operation of a cerebrospinal fluid management system causes the cerebrospinal fluid management system to initiate one or both of:
 a cooling treatment protocol; and
 a filtration treatment protocol.

16. A non-transitory computer readable medium having stored thereon a program code for use by a computing device, the program code causing the computing device to execute a method for managing inflammation comprising:
 determining a value related to one or more measurements of one or more physiological parameters;
 displaying a medical image of the patient in a selectable pane on a user interface, wherein the selectable pane is configured to be selected and what is displayed on the selectable pane is changed in response to the selectable pane being selected;
 displaying one or both of the measurements of the one or more physiological parameters of a patient and the value related to the monitored measurements of the one or more physiological parameters in a real-time updating pane on the user interface simultaneously with and adjacent to the selectable pane;
 comparing the value related to the one or more measurements of the one or more physiological parameters to a threshold value;
 selecting a predetermined treatment protocol from a database of predetermined treatment protocols; and
 outputting a control signal to adjust operation of a cerebrospinal fluid management system according to the selected predetermined treatment protocol based on the comparison of the value related to the one or more measurements of the one or more physiological parameters to the threshold value.

17. The non-transitory computer readable medium of claim 16, the method further comprising:
- determining a difference between the value related to the one or more measurements of the one or more physiological parameters and the threshold value;
- wherein the selecting the predetermined treatment protocol from the database of predetermine treatment protocols is based on the determined difference between the value related to the one or more measurements of the one or more physiological parameters and the threshold value.

18. The non-transitory computer readable medium of claim 17, wherein the predetermined treatment protocol is a treatment start protocol selected in response to the value related to the one or more measurements of the one or more physiological parameters reaching or going beyond the threshold value a first time.

19. The non-transitory computer readable medium of claim 17, wherein the predetermined treatment protocol is a treatment stop protocol selected in response to the value related to the one or more measurements of the one or more physiological parameters reaching or going beyond the threshold value.

20. The non-transitory computer readable medium of claim 17, wherein the predetermined treatment protocol is selected from the database of predetermined treatment protocols based on one or both of:
- a type of physiological parameter associated with the one or more measurements; and
- the comparison of the value related to the one or more measurements of the one or more physiological parameters to the threshold value.

\* \* \* \* \*